United States Patent
Nagai et al.

(12) 
(10) Patent No.: US 6,575,904 B2
(45) Date of Patent: Jun. 10, 2003

(54) BIODATA INTERFACING SYSTEM

(75) Inventors: Kazutoshi Nagai, Ikoma (JP); Motomichi Kato, Tenri (JP); Itaru Enguchi, Nara (JP); Toshiyuki Tanaka, Yamatokoriyama (JP); Naruaki Akai, Yamatokoriyama (JP); Masanori Nishikawa, Yamatokoriyama (JP); Kiyoshi Sekiya, Nara (JP); Shunichi Nagamoto, Nara (JP); Minoru Hotta, Kameoka (JP); Masaru Kikukawa, Itami (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/847,342

(22) Filed: May 3, 2001

(65) Prior Publication Data

US 2001/0047126 A1 Nov. 29, 2001

(30) Foreign Application Priority Data

| May 9, 2000 | (JP) | ................ 2000-135690 |
| Jul. 5, 2000 | (JP) | ................ 2000-135691 |
| Jul. 5, 2000 | (JP) | ................ 2000-203380 |
| Jul. 24, 2000 | (JP) | ................ 2000-222283 |
| Feb. 9, 2001 | (JP) | ................ 2001-033432 |

(51) Int. Cl.[7] ............................. A61B 5/00; G06F 1/16
(52) U.S. Cl. ................. 600/301; 128/903; 128/904; 206/499; 206/569; 345/169; 361/681
(58) Field of Search ........................... 600/300, 301, 600/454; 128/903, 904; 248/920; 345/156, 168, 169; 348/42; 396/263; 206/499, 569, 570; 361/681, 683

(56) References Cited

U.S. PATENT DOCUMENTS

| 4,608,994 A | | 9/1986 | Ozawa et al. | |
| 5,345,362 A | * | 9/1994 | Winkler | ............. 248/456 |
| 5,441,047 A | * | 8/1995 | David et al. | ............. 128/904 |
| 5,496,257 A | * | 3/1996 | Kelly | ............. 600/454 |
| 5,701,904 A | * | 12/1997 | Simmons et al. | ............. 348/42 |
| 5,865,745 A | | 2/1999 | Schmitt et al. | |
| 5,895,354 A | * | 4/1999 | Simmons | ............. 128/903 |
| 5,919,141 A | | 7/1999 | Money et al. | |
| 5,931,791 A | | 8/1999 | Saltzstein et al. | |
| 6,014,432 A | | 1/2000 | Modney | |
| 6,083,156 A | * | 7/2000 | Lisiecki | ............. 600/301 |
| 6,116,426 A | * | 9/2000 | Slonim | ............. 206/499 |
| 6,125,028 A | * | 9/2000 | Matsumoto | ............. 248/920 |
| 6,151,012 A | * | 11/2000 | Bullister | ............. 345/168 |
| 6,178,087 B1 | * | 1/2001 | Cho et al. | ............. 312/223.1 |
| 6,275,376 B1 | * | 8/2001 | Moon | ............. 345/168 |
| 6,400,903 B1 | * | 6/2002 | Conoval | ............. 396/263 |
| 6,504,706 B2 | * | 1/2003 | Stewart | ............. 345/169 |

FOREIGN PATENT DOCUMENTS

| EP | 0857456 | 8/1998 |
| JP | 2000-83907 | 3/2000 |

* cited by examiner

Primary Examiner—Eric F. Winakur
Assistant Examiner—David J. McCrosky
(74) Attorney, Agent, or Firm—Wenderoth, Lind & Ponack, L L P.

(57) ABSTRACT

A biodata interfacing device includes a service console, an attachment storage compartment defined in the service console for accommodating a variety of sensors used for collecting biodata, a lid mounted on the service console for opening and closing a top opening of the attachment storage compartment, and a display unit formed on an upper surface of the lid.

53 Claims, 16 Drawing Sheets

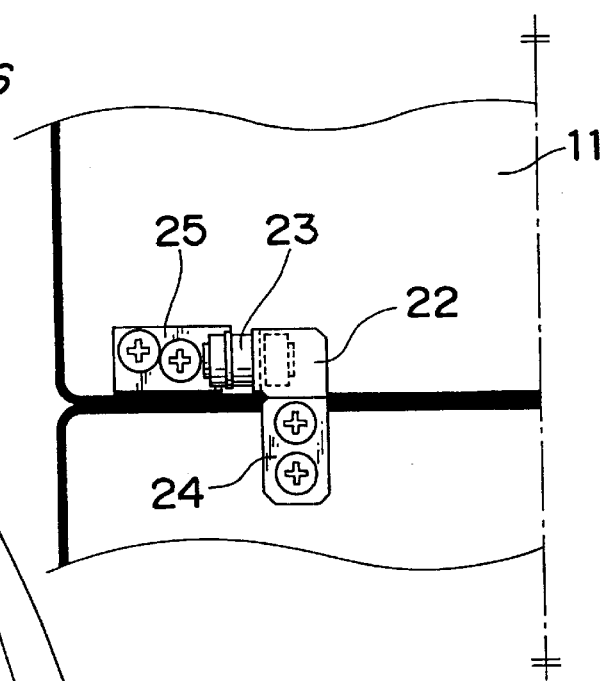
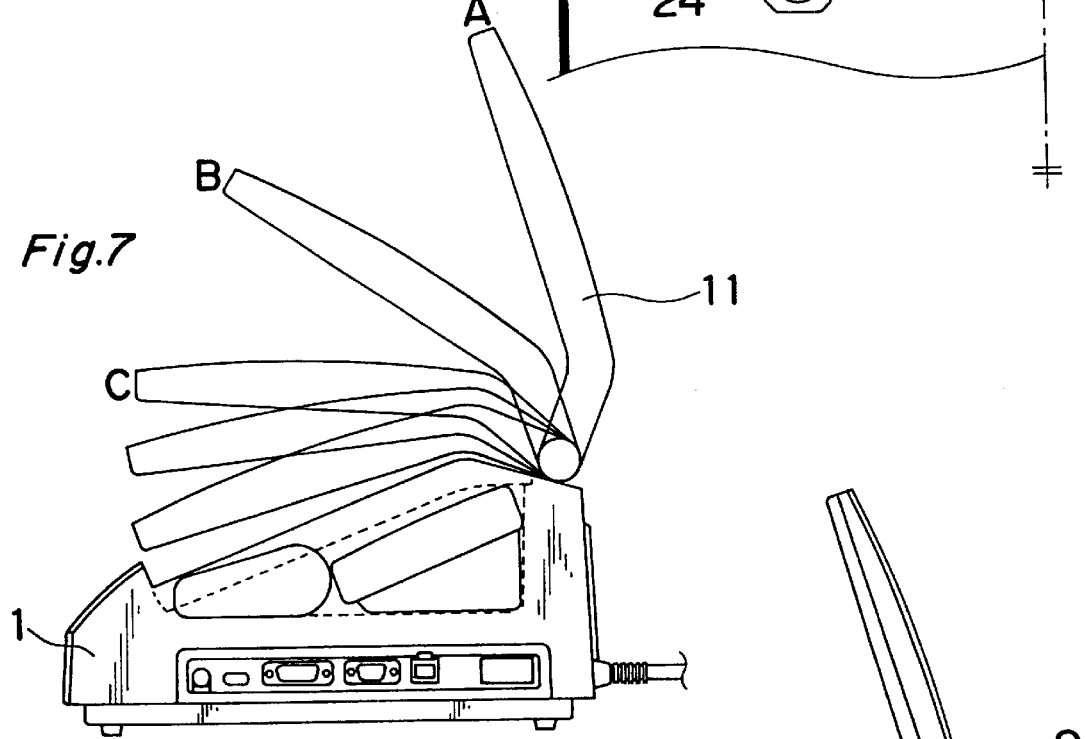
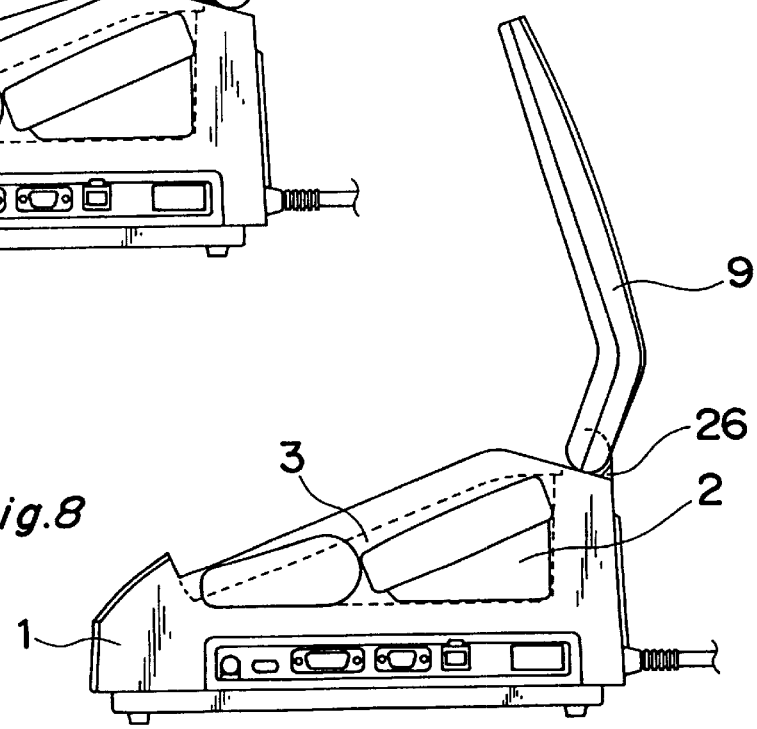

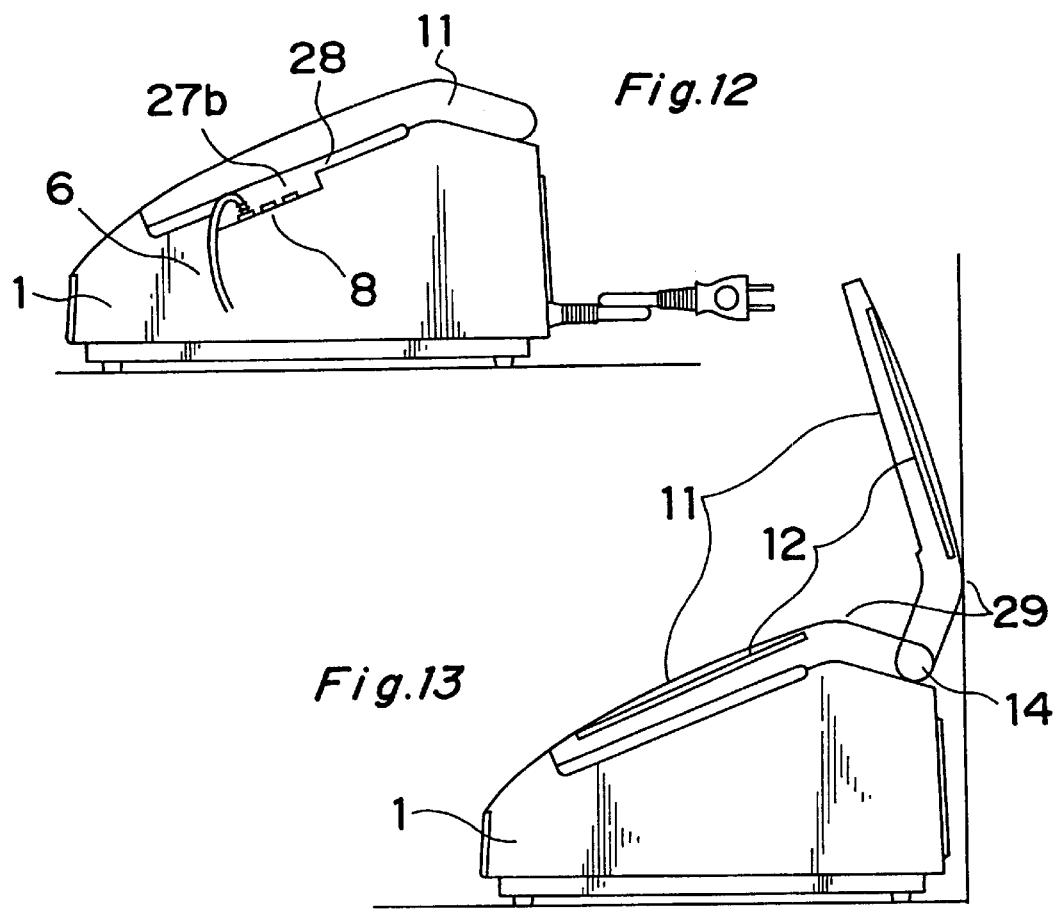
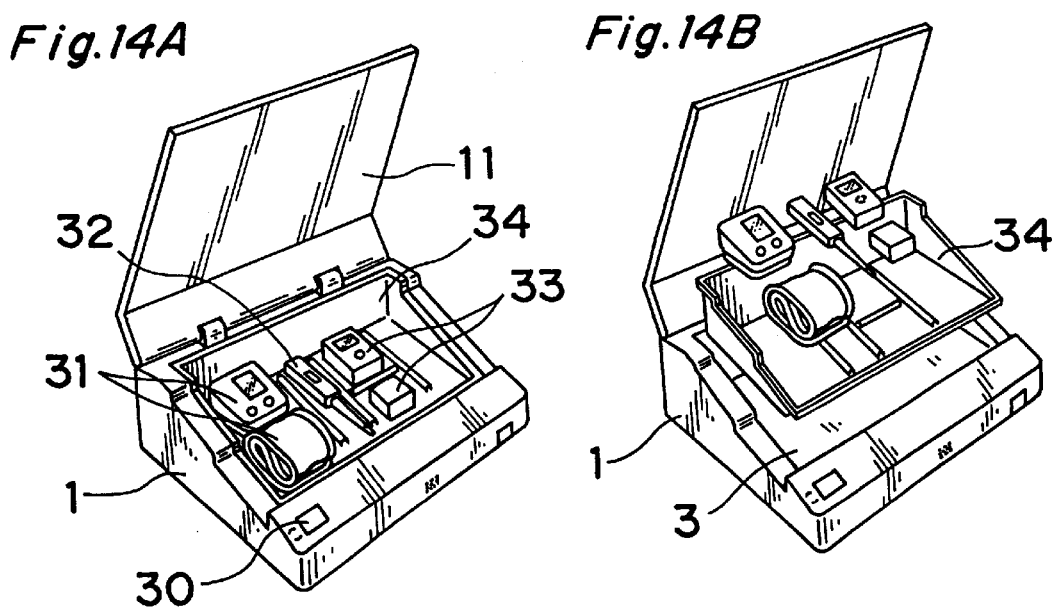

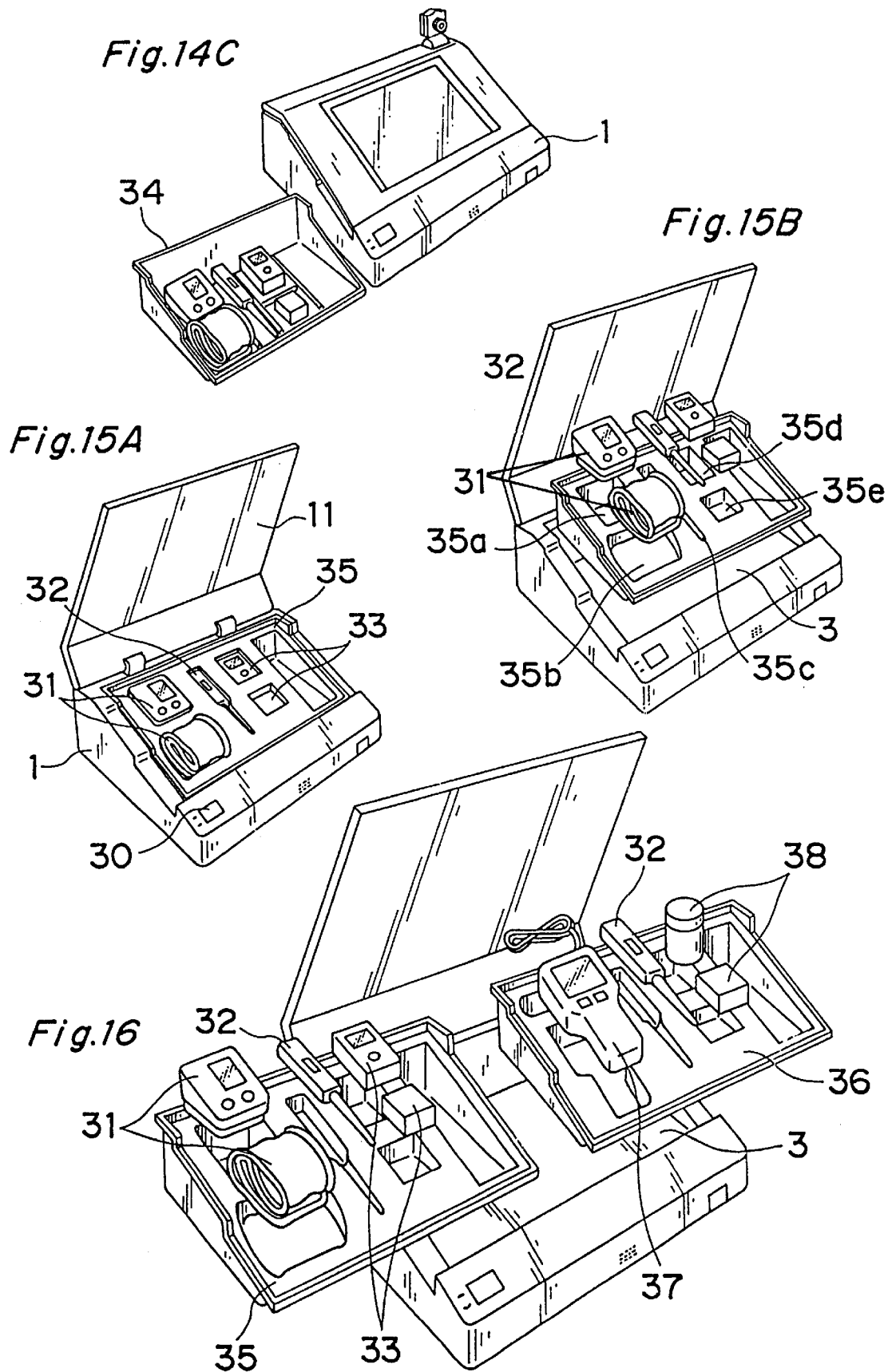

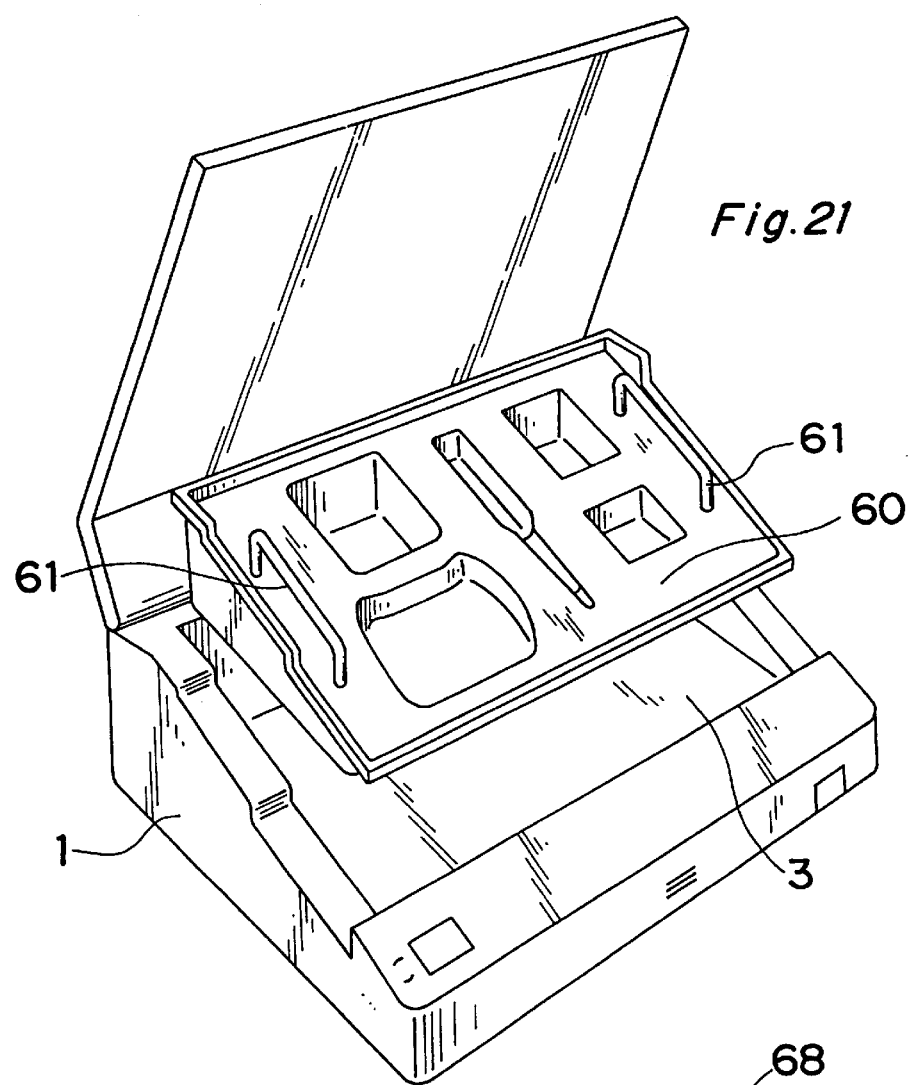
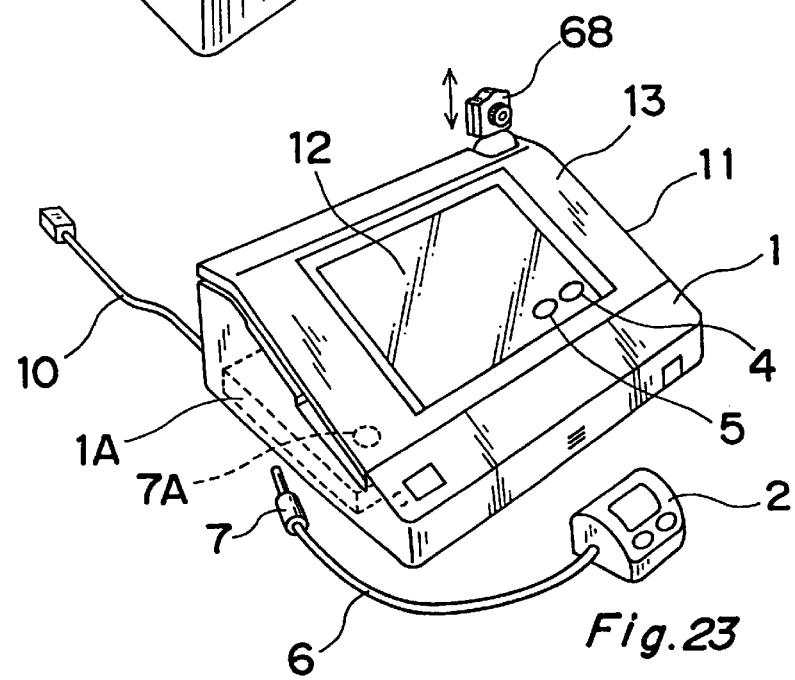

BIODATA INTERFACING SYSTEM

BACKGROUND OF THE INVENTION

1. Field of the Invention

The present invention generally relates to a home health care system and, more particularly to a health care information interfacing system including various sensors for collecting health care information, hereinafter referred to as biodata, from a patient or a user at home for use with regard to his or her own home health care and/or for transmission to a health care provider at a remote location for remote medical diagnosis.

2. Description of the Prior Art

Various biodata interfacing systems of a kind referred to above have been suggested. See, for example, U.S. Pat. No. 5,865,745, issued Feb. 2, 1999, and U.S. Ser. No. 6,014,432, issued Jan. 11, 2000. The exemplary biodata interfacing system is generally made up of two separated stations, a patient station and a health care provider station. The patient station includes various sensors for measurement of biodata such as, body temperature, blood pressure, pulsation, brain waves and/or heart beat of a patient at home, and a transmitter for transmitting, wireless or over a public telecommunication network, that biodata to a health care provider at a remote location. The patient station also includes a receiver and a display unit for receiving and displaying results of diagnosis and/or instructions from the health care provider, respectively. The biodata interfacing system is indeed efficient and convenient in that the patient need not visit the health care provider for measurement of the biodata and the health care provider can make a quick decision on the received biodata.

It is to be noted that the term "health care provider" hereinabove and hereinafter used is intended to encompass not only a hospital or a doctor, but also a health care or day-service nurse or any other person or facility commissioned or requested to take care of health and/or medical conditions of a patient or any other user of the patient station.

The standard patient station, hereinafter referred to as a home biodata interfacing device, will now be described with reference to FIG. 39. The biodata interfacing device shown therein includes a service console 201, various sensors for measurement of biodata on body temperature, blood pressure and pulsation, although only a clinical thermometer 202 is shown, a display unit 203 for providing visual presentation of measurements detected by the sensors and also for providing visual presentation of how to use the home biodata interfacing device, a lead line 204 connected between the clinical thermometer 202 and the service console 201 for transmitting a body temperature of the patient from the clinical thermometer 202 to the service console 201 and, optionally, a telephone line 205 for transmitting the biodata over a public telecommunication network.

When the home biodata interfacing device is in use, the patient or user (his or her family member or visiting health care nurse) at home can have the home body temperature measured with the thermometer 202, and the measured body temperature is then transmitted through the lead line 204 to the service console 201 from which it is subsequently displayed on the display unit 203 and/or transmitted to a health care provider over a public telecommunication network such as, for example, a public telephone system. The health care provider when receiving the measured body temperature of the patient from the service console 200 over the public telephone system may make at a remote location a diagnosis on health conditions of the patient. However, even if the telephone line 205 is not connected to the public telephone system, with a built-in transmitter held inactive, the service console 200 can serve the purpose of providing information to the patient and/or user.

The home biodata interfacing device now in use has a problem in that the patient and/or user have difficulty looking at the display window because the display unit 203 is not positioned in a fashion friendly to the patient and/or user.

In a certain home biodata interfacing device now in use, since the display unit and a lid or cover constitute members separate from each other, the home biodata interfacing device itself tends to be bulkier than necessary and is therefore less handsome in appearance, not easy to carry and inconvenient with regard to storage and transportation. Without the lid or cover, the sensors are exposed to the outside of the service console and this is objectionable in terms of hygienic aspects Also, unless the lid or cover is opened, no one can look at the display window. This is indeed inconvenient particularly where the home biodata interfacing device is to be used only for reconfirmation of past measurements without the sensors being used.

As a matter of design, the currently used home biodata interfacing device includes some operating buttons each allocated for one type of biodata measurement. The greater the number of the operating buttons, the more difficult and inconvenient for the user to input date through the operating buttons. If the operating buttons are arranged crowded in a limited area, an erroneous inputting (key-in) would be highly likely to occur. On the other hand, increase of the size of each operating button and/or increase of space between neighboring operating buttons, both in an attempt to minimize the erroneous inputting, would result in increase of the size of the service console.

A home biodata interfacing device is also known in which the display unit is incorporated into the lid or cover as is the case with a note-sized personal computer, and is configured to have a touch screen having a plurality of touch-sensitive areas functionally corresponding to keys in a keypad. Access to the touch screen can be made only when the lid or cover is opened or pivoted to an erected position. In such case, assuming that the lid or cover is held at the erected position that is at right angles or an obtuse angle to a console body, application of a finger pressure to a selected one of the touch-sensitive areas would often result in lifting of the console body above a support surface, for example, a desk top, and the service console including the console body and the display unit would eventually turn backwards.

Where the console body and the lid or cover is hingedly connected together, it is often observed that the home biodata interfacing device may be allowed to stand with the lid or cover left opened, in which case dust may pile up on the console body and/or water may spill onto the console body. This would lead to a detrimental problem with regard to the functionality of the home biodata interfacing device.

An additional problem is also pointed out in that if the lid or cover is excessively opened relative to the console body, connections between the lid or cover and the console body would be damaged.

Connector sockets for connecting the sensors to the console body are generally installed in one of opposite side walls of the console body so as to line up in a row extending front to rear. If one of the connector sockets closest to the user occupying a position in face-to-face relation with the erected display unit is occupied by a plug-in connector of one of the sensors, the user would experience difficulty looking and/or making access to the remaining connectors. This may lead to a difficulty or error in making connection between another plug-in connector with one of the remaining connector sockets. In addition, opening of the lid or cover would result in inadvertent collision with and, hence, damage to the home biodata interfacing device and/or an object situated rearwardly of the home biodata interfacing device.

While the home biodata interfacing device is designed to transmit the measured biodata over, for example, the public telephone system to the health care provider at a remote location so that the health care provider can make a diagnosis or examination with reference to the biodata presented to the health care provider station. It may, however, often occur that the health care provider cannot make a sufficient diagnosis because lack of a function available in the home biodata interfacing device. By way of example, it may often occur that the health care provider may wish to secure biodata such as the patient's complexion, condition of the wound or skin that cannot be expressed with numerical values. In such case, the home biodata interfacing device would require an extra audio and/or video transmission device for transmitting audio and/or video information that enables the health care provider to listen to and/or view the conditions of the patient through audiovisual equipment at the health care provider station.

Furthermore, the home biodata interfacing device would be highly needed by aged people living depopulated areas, and most of those aged people are less familiar with how to handle medical home equipment and computer terminals. On the other hand, some of the medical equipment such as, for example, a cardiograph or stethoscope of a kind a doctor or nurse applies directly to a patient would give rise to erroneous data when the patient himself or herself uses it for data acquisition. To avoid this possibility, the patient or user has to review the how-to description or manual.

However, it would not be easy for aged, but presbyopic people to look not only at the how-to description or manual, but also legends embossed or printed in the home biodata interfacing device to indicate types of connector sockets. Erroneous manipulation and line connection would result in presentation of erroneous biodata and, therefore, the health care provider would not be able to make an accurate diagnosis.

SUMMARY OF THE INVENTION

With the numerous disadvantages and inconveniences found in the existing home biodata interfacing device, an object of the present invention is to provide a home biodata interfacing device of a kind which is stable, compact in size, and easy to use and in which a display unit is easy to view.

Another object of the present invention is to provide a home biodata interfacing device which has a large capacity of accommodating various sensors easily and is hygienically acceptable without allowing the sensors to be contaminated with dust.

A further object of the present invention is to provide a highly reliable home biodata interfacing device that can transmit various biodata including audio and/or video information to a remote location assuredly.

A still further object of the present invention is to provide a home biodata interfacing device having an increased operativity which is effective to avoid erroneous manipulation and erroneous line connection.

In order to accomplish these and other objects and features of the present invention, there is provided a biodata interfacing device which includes a service console, an attachment storage compartment defined in the service console for accommodating a variety of sensors used for collecting biodata, a lid mounted on the service console for opening and closing a top opening of the attachment storage compartment, and a display unit formed on an upper surface of the lid. Since the display unit is formed on the upper surface of the lid, the user can readily and easily look at the display unit and, accordingly, the biodata interfacing device can be conveniently manipulated by the user.

Also, the biodata interfacing device can be assembled compact and lightweight and, accordingly, numerous conveniences can be appreciated by the user in that the biodata interfacing device can be easily transported from place to place and can be stored in a relatively small space. At the same time, any possible contamination of the sensors is prevented to increase the hygienic factor.

The user can look at the display unit even though the lid is closed, i.e., in position to close the top opening of the instrument storage compartment in the service console, and the biodata interfacing device itself can be used not only for transmitting the biodata to the health care provider at a remote location, but also for reconfirming past biodata and/or acknowledging a time of dosage of medicines without the sensors being used.

Preferably, the lid is configured to incline downwardly towards a position of a user of the biodata interfacing device so that user's viewing the information displayed can be facilitated along with increase in operativity of the biodata interfacing device.

The display unit may additionally include a touch panel. The additional use of the touch panel is effective to reduce the number of operating buttons which would otherwise be required, resulting in compactness of the biodata interfacing device as a whole along with increase of operativity thereof. Also, the possibility of the biodata interfacing device turning backward when a pushing force is horizontally applied is eliminated to thereby increase stability of the biodata interfacing device.

The use of a recess that results in a partial increase of a gap between the service console and the lid is effective to avoid any possible biting of a connecting cable extending between the service console and an external sensor which would otherwise hamper a complete closure of the lid, and which would otherwise result in damage to the connecting cable.

The service console may have a terminal unit provided on an upper surface of the service console and through which the sensors positioned externally of the service console communicate with the service console. This is particularly advantageous and effective to avoid such a problem in that if one of the connector sockets closest to the user occupying a position in face-to-face relation with the erected display unit is occupied by a plug-in connector of one of the sensors, the user would experience difficulty in looking at and/or accessing the remaining connectors.

The service console and the lid are preferably connected to each other through a hinged connection about which the lid pivots relative to the service console. In such case, if the hinged connection has a damping mechanism, the lid once opened will not be left opened and, accordingly, there is no possibility of dust piling up inside the service console and also of water spilling into the service console.

Where a projection, operable to interfere with the service console to limit a pivotal movement of the lid before the lid is pivoted to a limit defined by a hinged connection between the lid and the service console, is provided in either the lid or the service console, any possible damage to the hinged connection can advantageously be avoided.

The biodata interfacing device of the present invention is preferably provided with an instrument canister enabling the sensors to be accommodated within the attachment storage compartment in a form as accommodated in the instrument canister. The use of the instrument canister is particularly advantageous in that plural sensors can be removed from the attachment storage compartment all at a single time and, on the other hand, the plural sensors can be stored in an orderly fashion as accommodated in the instrument canister.

The instrument canister may have a plurality of pockets each contoured to correspond to the shape of a respective sensor so that the sensors can be snugly accommodated within dedicated recesses in the instrument canister. Once the sensors are accommodated within the associated pockets, the sensors will not arbitrarily move and/or collide against each other within the service console during, for example, transportation of the biodata interfacing device from place to place and, therefore, any possible damage to the sensors can advantageously be eliminated. Also, even though the instrument canister is removed from the instrument storage compartment, the sensors remain orderly arranged in the instrument canister.

The instrument canister may include a plurality of in-box trays each for accommodating a particular combination of the sensors. In such case, in the event that the combination of the sensors changes to another combination, replacement of one in-box tray accommodating the current combination of the sensors with another in-box tray accommodating the new combination of the sensors is sufficient to enable the new combination of the sensors to be accommodated within the instrument storage compartment through such another in-box tray. Accordingly, if the plural in-box trays accommodating different combinations of the sensors are made available, a single biodata interfacing device can be utilized using the sensors of a different combination merely by replacing the in-box tray with another one.

Alternatively, the instrument canister may include a plurality of in-box trays each for accommodating one of the sensors. In such case, even when change occurs in one of the sensors, replacement of the in-box tray used to accommodate such one of the sensors is sufficient to accommodate a new sensor.

The instrument canister may include at least one pair of grooves in combination with a partitioning structure removably engaged in the grooves to define a partition room corresponding in shape to a shape of one of the sensors. In such case, repositioning the partitioning structure is effective to increase or decrease the volume of partition room in the instrument canister to suit to the shape of a particular sensor with no cost incurred.

The instrument canister may have at least a portion thereof capable of being stacked in a direction heightwise thereof. In such case, the number of the sensors each having a relatively small thickness that can be accommodated in the instrument canister can be increased to thereby maximize the limited space available in the instrument canister. The capability of accommodating the increased number of the sensors brings about an advantage in that the biodata interfacing device can be used by those who require use of as many sensors as possible, without the size of the biodata interfacing device being increased.

If a space is defined between the instrument canister and the attachment storage compartment in the service console, the sensors will not be adversely affected by heat evolved from electronic component parts built into the service console, and are therefore substantially free from thermal stresses. This means that the sensors can be kept thermally stable, resulting in accurate measurement of biodata from the patient.

The instrument canister may be provided with a handle for facilitating removal thereof from the attachment storage compartment.

Preferably, the instrument canister is provided with identifying structure for identifying a type of the instrument canister, which cooperates with a reading device provided in the service console for reading the identifying structure. In such case, a mode override structure built into the service console will change a mode of operation of the biodata interfacing device according to a result of reading of the identifying structure by the reading device. Replacement of the instrument canister can effectively select one of the operating modes automatically and, therefore, no manual changeover operation is required even when a combination of the sensors is changed.

Again, the biodata interfacing device of the present invention may be equipped with a camera unit. This camera unit is preferably detachably provided on an outer surface of the service console. The use of the camera unit enables transmission of an image of the complexion of the patient together with transmission of the measured biodata to the health care provider at a remote location. The camera unit can also be used for imaging an affected region of the patient when removed from the service console.

A microphone if desired may be provided in the service console, so that voiced explanation of, for example, the affected zone of the patient can be transmitted together with the image captured by the camera unit, if so required by a doctor.

In order for the camera unit to be used in image capture at any location without the position of the biodata interfacing device being changed, the camera unit is preferably pivotable at a mounting area on an outer surface of the service console. Detachment of the camera unit from the service console may be carried out by a holder provided in the camera unit, and an engagement provided on the outer surface of the service console that is detachably engageable with the holder. Also, the camera unit may be pivotally engaged in a holding portion, and alternatively or in combination therewith, the holder of the camera unit has a grip defined therein which a user can grip externally. If this grip is of a generally cylindrical shape and is detachable by inserting it into a recess formed in the outer surface of the service console, not only can the user grip the camera unit comfortably, but also the camera unit can be aimed in any direction conveniently.

Alternatively, the camera unit may include a camera body and a camera support, with the camera body being removably mounted on the camera support.

Arrangement may also be made so that at least one of the camera body, the camera support and the holder can be accommodated within the instrument storage compartment when they are not in use.

The microphone is preferably of a type capable of receiving both a human voice and a voice signal from a sensor positioned in the vicinity of the microphone. Where the microphone is used, the microphone is preferably enclosed by an elastic member which is in turn fixed inside the service console. The use of the elastic member is effective to minimize transmission of external noises or vibrations to the microphone and, accordingly the microphone can transmit a voice signal noiselessly.

A voice outputting instrument may be supported by a support member disposed in front of the microphone for supporting a sensor for outputting a voice signal. This is particularly advantageous if the user needs to hold the voice outputting instrument in his or her hand when transmitting voices thereto and, therefore, noiseless transmission of voices is possible.

Preferably, the support member disposed in front of the microphone is removable or slidable according to a shape of the sensor for outputting the voice signal. This support member can be removed and stored somewhere when no voice outputting instrument is needed in the biodata interfacing device. Accordingly, the presence of the support member will not provide an obstruction nor an eyesore. Moreover, even if the size of the voice outputting instrument changes to a smaller or larger one, the support member when slidable is effective to accommodate such smaller or larger voice outputting instrument.

The biodata interfacing device in one embodiment of the present invention may include a main control unit, a plurality of sensors for collecting biodata from a patient and converting them into physical signals, a terminal unit including a plurality of connecting terminals corresponding respectively to the sensors and for transmitting the biodata therefrom to the main control unit, and an operating unit and a display unit for interfacing the main control unit and a user for performing communication therebetween. When the user selects one of the sensors through the operating unit, the main control unit makes use of the display unit to provide the user with an indication of one of the connecting terminals of the terminal unit which corresponds to the selected sensor.

The biodata interfacing device in another embodiment of the present invention may include a main control unit, a plurality of sensors for collecting biodata from a patient and converting them into physical signals, a terminal unit including a plurality of connecting terminals corresponding respectively to the sensors and for transmitting the biodata therefrom to the main control unit, an operating unit through which a user communicates with the main control unit, and a plurality of light emitting diodes disposed adjacent the connecting terminals. When the user selects one of the sensors through the operating unit, the main control unit has a function of turning on one of the light emitting diodes which corresponds to the selected sensor.

The biodata interfacing device in a further embodiment of the present invention may include a main control unit, a plurality of medical measuring instruments for collecting biodata from a patient and converting them into physical signals, a terminal unit including a plurality of connecting terminals corresponding respectively to the medical measuring instruments and for transmitting the biodata therefrom to the main control unit, an operating unit and a voice output unit through which a user communicates with the main control unit. When the user selects one of the medical measuring instruments through the operating unit, the main control unit makes use of the voice output unit to provide the user with an audio indication of one of the connecting terminals of the terminal unit which corresponds to the selected medical measuring instrument.

In any case, the terminal unit preferably has a plurality of connecting terminals and a plurality of colored indications, one for each of the connecting terminals and disposed adjacent the connecting terminals, and the main control unit has a function of informing the user through the display unit of one of the colored indications that corresponds to the selected sensor. Alternatively or in combination therewith, each of the sensors comprises a sensor body and a connecting cable for electrically connecting the sensor body to the connecting terminal. A portion of the sensors are colored in a predetermined color, and the terminal unit has respective portions adjacent the associated connecting terminals that are colored in different colors corresponding to respective colors of those portions of the sensors.

Again, alternatively or in combination therewith, the connecting cables of the sensors may have different shapes and the connecting terminals of the terminal unit have correspondingly different shapes, such that only when the shapes of one connecting cable and a corresponding terminal match with each other can the connecting cable and a corresponding terminal member be electrically connected together.

BRIEF DESCRIPTION OF THE DRAWINGS

The present invention will become readily understood from the following description of preferred embodiments thereof made with reference to the accompanying drawings, in which like parts are designated by like reference numeral and in which:

FIG. 6 is a schematic diagram showing one hinged connection between the lid and a service console, both forming parts of the home biodata interfacing device of the present invention;

FIG. 7 illustrates how the lid moves when the hinged connection shown in FIG. 6 is employed;

FIG. 8 is a view similar to FIG. 7, showing a first modification of the home biodata interfacing device;

FIGS. 9 to 13 are schematic side views of the home biodata interfacing device showing second to sixth modifications thereof, respectively;

FIG. 14A is a schematic perspective view of the home biodata interfacing device according to a second preferred embodiment of the present invention, with an in-box tray shown as nested with in the service console;

FIG. 14B is a view similar to FIG. 14A, showing the in-box tray as floated above the service console;

FIG. 14C is a view similar to FIG. 14A, showing the in-box tray removed from the service console;

FIGS. 15A and 15B are views similar to FIGS. 14A and 14B, respectively, showing a first modification of the second embodiment;

FIG. 16 is a schematic perspective view of the home biodata interfacing device according to a second modification of the second embodiment with two in-box trays shown;

FIG. 21 shows an in-box tray having handles;

FIG. 23 is a schematic perspective view of the home biodata interfacing device according to a third preferred embodiment of the present invention;

DESCRIPTION OF THE EMBODIMENTS

Figure 1:
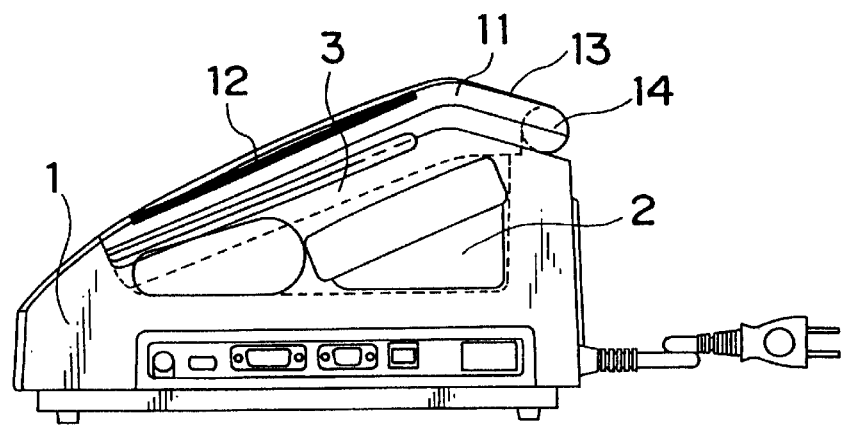
FIG. 1 is a side view, with a portion removed, of a home biodata interfacing device according to a first preferred embodiment of the present invention.

Referring first to FIGS. 1 to 4, in a preferred embodiment of the present invention, a home biodata interfacing device shown therein includes a service console 1, an attachment storage compartment 3 for neatly accommodating a plurality of, for example, body temperature and blood pressure sensors 2 and other miscellaneous accessories, a data transmission switch 4 that is used when collected biodata are desired to be transmitted to a health care provider, and an input switch 5 that is used when numerical values are to be inputted.

Reference numeral 6 represents a connection cable for connecting one of the sensors 2 with the service console 1. This connection cable 6 has its opposite ends provided with a respective connector plug 7 and is used for transmitting biodata collected by the sensor 2 to the service console 1. The service console 1 has a plug-in socket 8 for receiving one of the connector plugs 7 of the connection cable 6 whereas each of the sensors 2 has a corresponding plug-in socket 9 for receiving the other of the connector plugs 7 of the connection cable 6.

Figure 4:
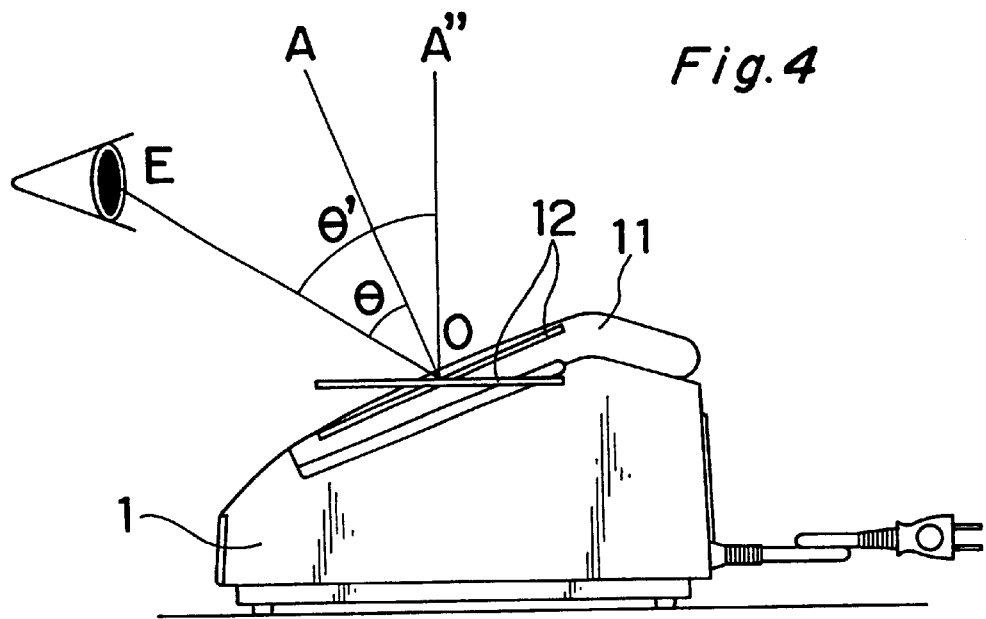
FIG. 4 is a schematic side view of the home biodata interfacing device shown in FIG. 1, showing how a display panel is viewed.

Similarly, reference numeral 10 represents a telephone cable that is used when the biodata collected by the service console 1 are to be transmitted to the health care provider at a remote location over a public telephone system and is of a structure similar to the connection cable 6, having its opposite ends provided with a respective connector plug 7. The service console 1 also includes a pivotally supported lid 11 mounted atop the service console 1 for movement between closed and opened positions about a hinge axis defined by one or more connecting members 14, for example, hinges. The lid 11 has outer and inner surfaces opposite to each other and includes a liquid crystal display panel 12 provided in the outer surface thereof together with a display support frame 13 for supporting it. The lid 11 when held in the closed position as shown in FIGS. 1 and 4 covers the attachment storage compartment 3 with the liquid crystal display panel 12 remaining exposed to the outside.

Figure 3:
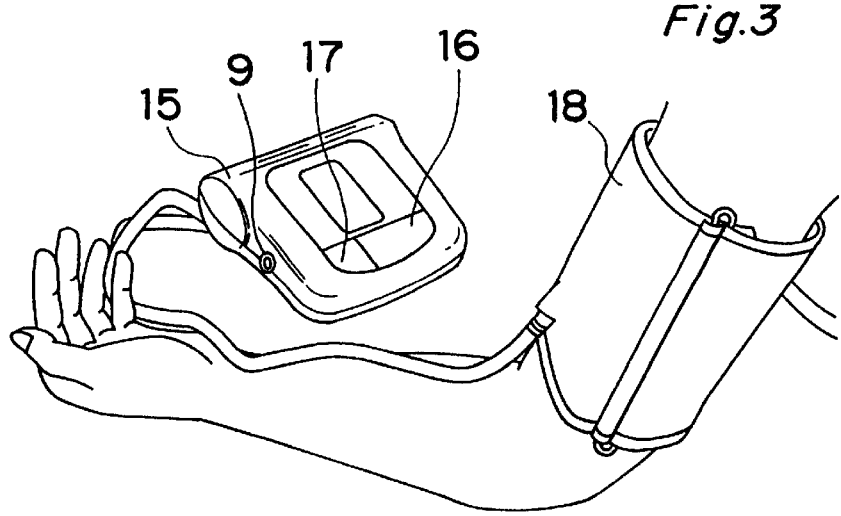
FIG. 3 is a schematic diagram showing how blood pressure is measured with use of an electronic sphygmomanometer forming a part of the home biodata interfacing device.

One example of the sensors 2 is an electronic sphygmomanometer (blood pressure gauge) 15 shown in FIG. 3. This electronic sphygmomanometer 15 includes a casing provided with a measurement button 16 and a transmission button 17 that is used when biodata measured thereby are desired to be transmitted, a manchette or cuff 18 that is placed around an arm during blood pressure measurement, and the plug-in socket 9 for receiving the connector plug 7 leading from the connection cable 6.

The home biodata interfacing device of the structure described above can be used in the following manner. When ae patient or his or her family member wishes to collect biodata of the patient for transmission to the health care provider at a remote location so that he or she can receive a medical examination or diagnosis from the health care provider, a necessity arises for the user to use the sensor 2. In that case, as the lid 11 is pulled upwards to allow it to be pivoted from the closed position towards the opened position about the hinge axis, the sensor 2 is exposed to his or her field of sight and the user can readily remove the sensor 2 from the attachment storage compartment 3. In the description that follows, reference will be made to the use of the electronic sphygmomanometer 15 as the sensor 2.

When the user wishes to perform a blood pressure measurement, he or she has to mount the cuff 18 around his or her or patient's arm at an appropriate location. Subsequent manipulation of the measurement button 16 results in activation of a pump (not shown) in the electronic sphygmomanometer 15 to inflate the cuff 18 to thereby apply a pressure to the arm. The pump is automatically halted when the applied pressure attains a predetermined value, with air inside the cuff 18 leaking through a reducing valve accompanied by a minute variation of pressure inside the cuff 18 under an influence of pulsation. By detecting this minute pressure variation, the blood pressure can be measured in a manner known to those skilled in the art. After the blood pressure measurement, the user has to connect the connector plugs 7 of the connection cable 6 to the corresponding plug-in sockets in the electronic sphygmomanometer 15 and the home biodata interfacing device 1, followed by manipulation of the transmission button 17 to cause the measured blood pressure to be transmitted from the electronic sphygmomanometer 15 to the home biodata interfacing device. Subsequent connection of the telephone cable 10 with a public telephone system followed by manipulation of the transmission switch 4 results in transmission of the blood pressure over the public telephone system to the health care provider at a remote location.

As is well known to those skilled in the art, when the user views the screen of the display panel in a direction at right angles thereto, images of a high contrast ratio and high brightness with minimized color variation can be viewed. This is generally true regardless of whether the display unit is comprised of a liquid crystal panel or a cathode ray tube. Referring particularly to FIG. 4, assuming that the position of the eyes of the user is expressed by E, an arbitrarily chosen point on the display panel 12 is expressed by O, and the direction normal to the display panel 12 and passing through the point O is expressed by a line A. The smaller the angle θ bound by the line A and a line drawn between the position E and the point O, the higher the viewability. This angle θ is of course zero when the display panel 12 is viewed exactly along the direction normal to the display panel 12.

In FIG. 4, a line shown by A" represents the direction normal to the display panel 12 when the display panel 12 is held horizontally. In this case, the angle θ" between the line A" and a line drawn between the position E and the point O is greater than the angle θ.

In view of the foregoing, if the lid 11 carrying the display panel 12 is so designed and so configured as to incline downwardly in a direction towards the position of the user, the display panel 12 capable of providing a high viewability with high contrast and highly bright images presented to the eyes of the user can be obtained as compared with the lid 11 not inclined downwardly towards the position of the user, making it possible to provide conveniences for the benefit of the user.

In the foregoing description, the transmission switch 4 and the input switch 5 have been described as mechanically installed. However, both may be superseded by touch-sensitive areas of a touch panel disposed on the display panel 12. Each of the touch-sensitive areas of the touch panel is of a structure including two electrodes disposed in face-to-face relation with each other with a gap defined therebetween by virtue of a spacer interposed therebetween. When the user applies a finger pressure externally to the touch-sensitive area, a surfacing material thereof is elastically deformed to cause the electrode on an upper surface to be connected with the electrode on a lower surface to close an electric circuit therebetween. At any point on the touch panel, a peculiar voltage can be detected at the point of contact between the electrodes and can provide an indication of the position. This is the principle of the touch panel.

Figure 5:
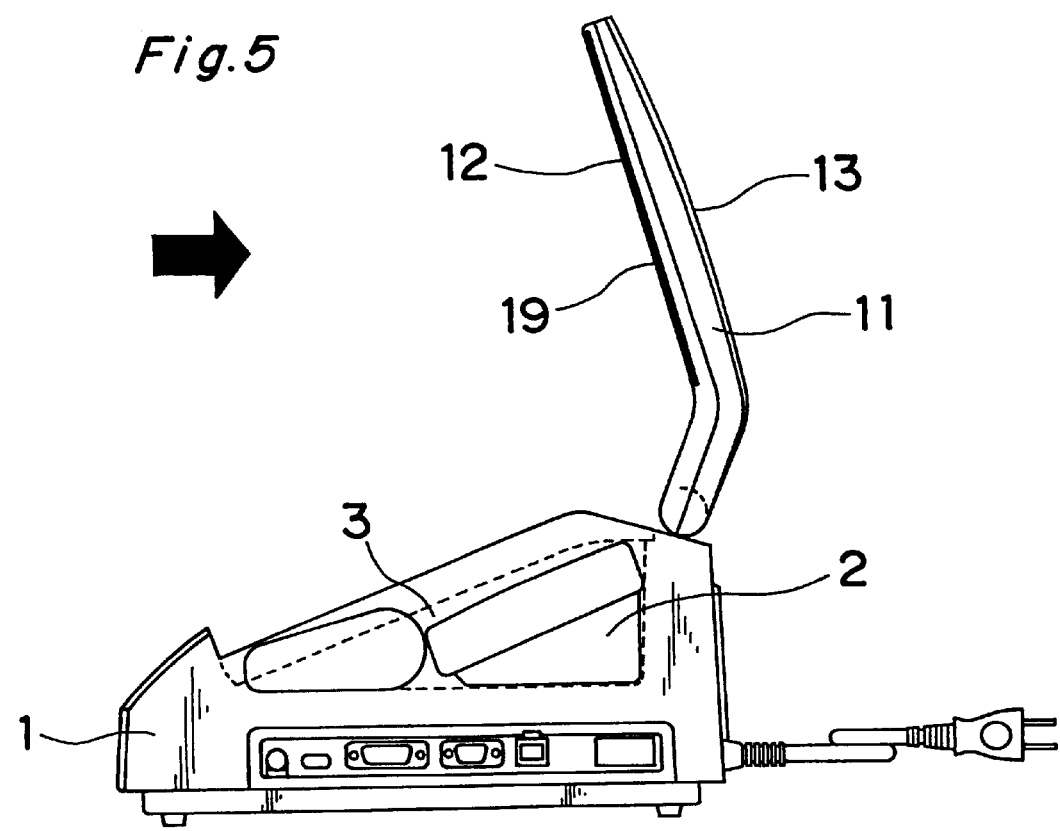
FIG. 5 illustrates the home biodata interfacing device taken only for the purpose of discussion of how the display unit works when installed on an inner surface of a lid of the interfacing device.

In the case of an existing note-sized personal computer, a touch panel 19 disposed on the display panel is located on an inner surface of the lid. In such case, as shown in FIG. 5, when a finger pressure is applied horizontally to a selected one of the touch-sensitive areas of the touch panel 19 while the lid 11 is opened, the lid 11 in the opened position would be tilted backwards with the service console 1 tending to be lifted upwardly and, in the worst case, the biodata interfacing device itself would eventually turn backwards.

However, in the illustrated embodiment, the display panel 12 is disposed on the outer surface of the lid 11 and the touch panel is mounted on the display panel 12 so as to be directed outwardly of the home biodata interfacing device particularly when the lid 11 is in the closed position. Accordingly, this ensures a stability of the home biodata interfacing device that is free from the inconvenience which would otherwise result from by the horizontal application of the finger pressure as discussed hereinabove.

Figure 2:
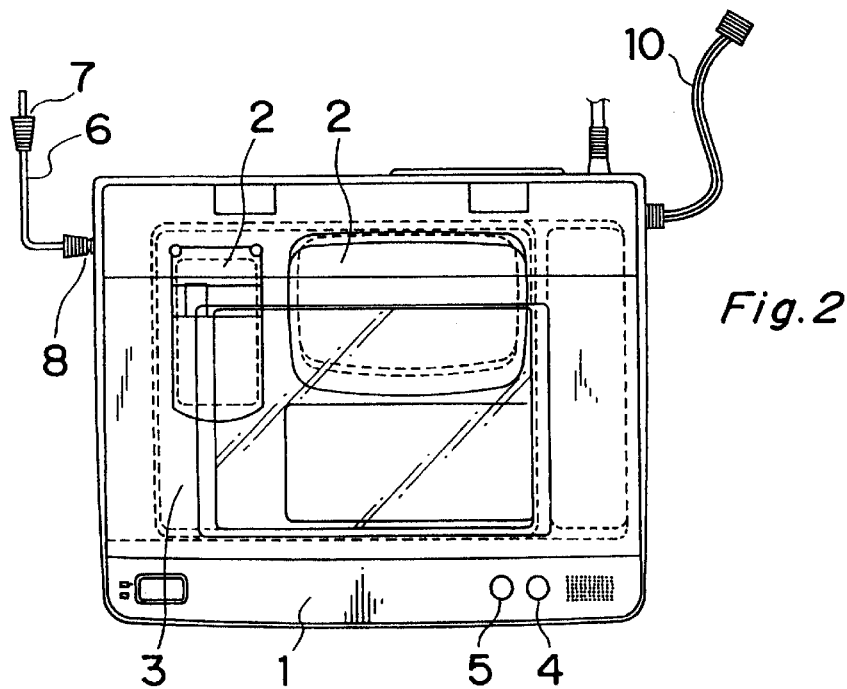
FIG. 2 is a top plan view of the home biodata interfacing device shown in FIG. 1.

FIG. 6 illustrates one of hinged connections between the service console 1 and the lid 11 that are employed in the home biodata interfacing device shown in FIGS. 1 and 2. In this figure, reference numeral 22 represents a hinge made up of a hinge pin 23 and first and second hinge members 24 and 25 mounted pivotally around the hinge pin 23 and fixedly connected respectively with the service console 1 and the lid 11. The first hinge member 24 is secured to the service console 1 by set screws while the second hinge member 25 is fixedly connected to the lid 11 by set screws, to thereby pivotally connect the lid 11 to the service console 1. The hinge pin 23 has a damping mechanism.

Referring now to FIG. 7, at positions A and B, the lid 11 can be held still there having been supported by the hinge 22. However, at any position below the position C, by the effect of the damping mechanism built in the hinge pin 23, the lid 11 can pivot about the hinge pin 23 in a direction, for example, counterclockwise as viewed therein, under the influence of a gravitational force until the lid 11 comes to assume the closed position.

Although in this embodiment the damping mechanism has been described as built in the hinge pin 23, a similar effect can be obtained even though the damping mechanism is independent of the hinge pin 23. All that is necessary is structure by which the lid 11 can be closed assuredly by the effect of its own weight.

As shown in FIG. 8, the lid 11 is provided with a positioning projection 26 movable together with the lid 11. In the event that the patient or user pulls the lid 11 upwards to open the lid 11 in readiness for removal or storage of the sensor 2 from or into the service console 1, no problem would occur if the amount of movement of the lid is usual and the lid 11 will not interfere with the positioning projection 26. However, if the amount of movement of the lid 11 is too excessive, exceeding a certain limit, the positioning projection 26 will interfere with the service console 1 to thereby prevent the lid 11 prematurely from being damaged. In this way, reliability can be increased. It is to be noted that although the positioning projection 26 has been described as formed in the lid 11, it may be formed on the service console 1.

Figure 9:
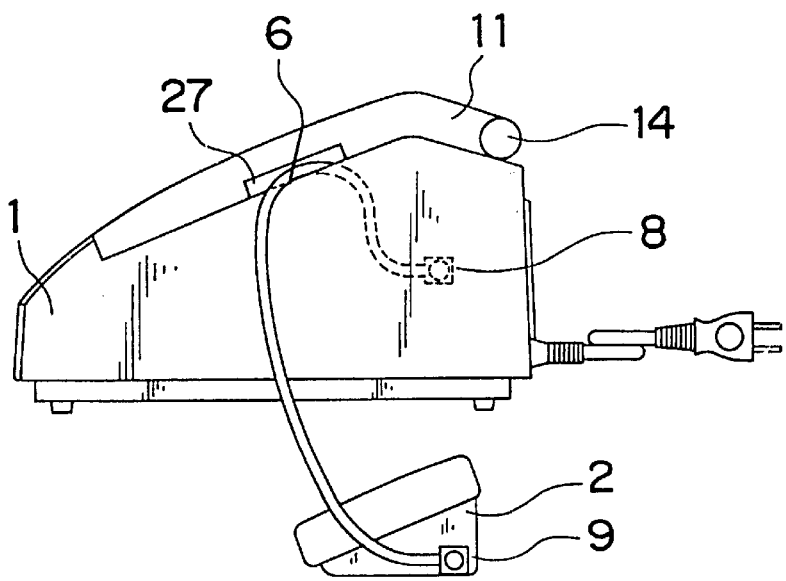

As best shown in FIG. 9, one of opposite side walls of the lid 11 is formed with a recess 27 for passage therethrough of the connection cable 6. It will often occur that the patient or user may use the home biodata interfacing device with the connection cable 6 left connected between the service console 1 and the sensor 2. In such case, the connection cable 6 is necessarily drawn out from the service console 1 for connection to the sensor 2. Without the recess 27 formed in the side wall of the lid 11, the connection cable 6 extending outwardly from the service console 1 would be bitten between the lid and the service console 1.

However, the presence of the recess 27 in the side wall of the lid 11 is advantageous in that the possibility of a portion of the connection cable 6 being bitten can be avoided. Consequently, not only can the lid 11 be smoothly pivoted relative to the service console 1, but any possible damage to the connection cable 6 including breakage thereof can advantageously be avoided to thereby eliminate erroneous data transmission, and, hence, reliability and a lifetime of the home biodata interfacing device can be increased.

Figure 10:
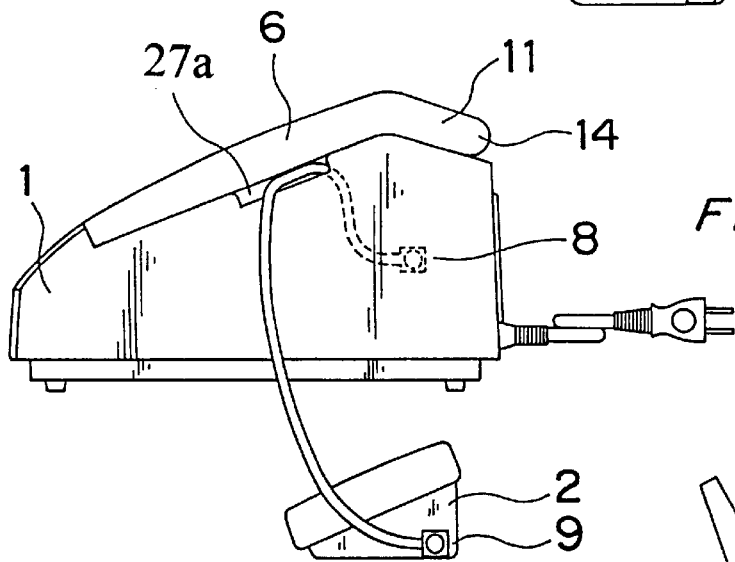

It is to be noted that in place of the recess 27 formed on the side of the lid 11, a recess 27a may be formed in an arbitrarily chosen angled portion of the service console 1 as shown in FIG. 10. In such case, the connection cable 6 connected to the plug-in socket 8 in the service console 1 extends outwardly through the recess 27a and is then connected with the plug-in socket 9 in the sensor 2.

Figure 11:
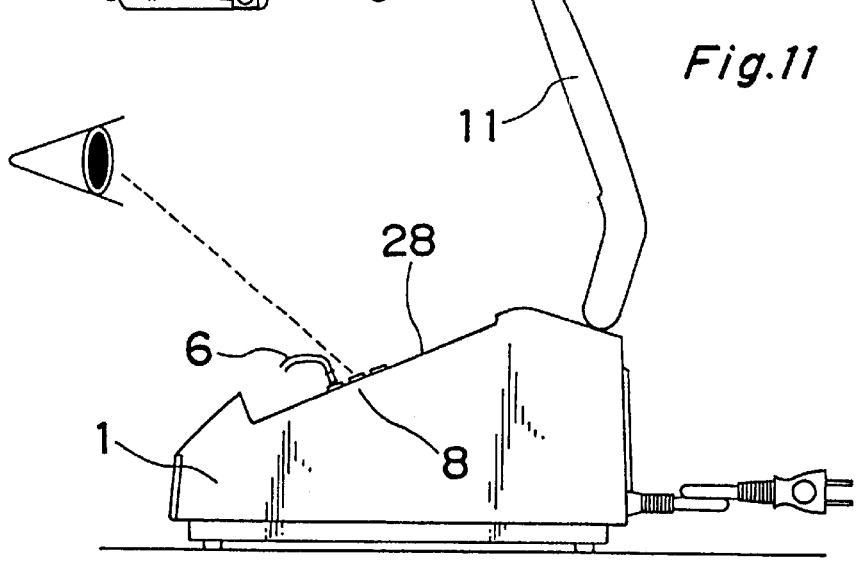

In a preferred embodiment, as shown in FIG. 11, plug-in sockets 8 may be disposed on an inclined top surface of the service console 1 that inclines downwardly from a position where the lid 11 is hinged towards the position of the user, so that the user can readily recognize respective positions of connectors substantially with a single glance.

Accordingly, it is possible not only to increase viewability and operativity, but also to avoid damage to the device and erroneous collection of biodata, both of which would otherwise result from erroneous connections.

Alternatively, as shown in FIG. 12, an inclined top surface 28 of the service console 1 may be formed with a recess 27b and plural plug-in sockets 8 are formed in this recess 27b. In this arrangement, not only can viewability of positions of connectors be increased, but also insertion of the connection cable 6 into one of the plug-in sockets 8 in the service console 1 is possible even while the lid 11 is held at the closed position.

The lid 11 will further be described in detail with particular reference to FIG. 13. With the lid 11 held at the closed position, the lid 11 represents a generally hill-like shape with a vertex 29 defined and positioned forwardly of the connecting members 14. In other words, front and rear regions of the lid 11 on respective sides of the vertex 29 are inclined downwardly from the vertex 29.

Assuming that the home biodata interfacing device embodying the present invention is placed on a support surface, for example, a desk top, which is placed against a wall, so as to occupy a position adjacent the wall as shown in FIG. 13, as the user pulls the lid 11 upwards to pivot the latter from the closed position towards the opened position, the vertex 29 of the lid 11 will be brought into contact with the wall the moment the opening of the lid 11 attains a predetermined value. Once the vertex 29 of the lid 11 is brought into contact with the wall, the lid 11 is no longer pivoted. Accordingly, the display panel 12 occupying a position on the downwardly inclined front region of the outer surface of the lid 11 will not be damaged, which would otherwise occur when it collides against the wall.

A home biodata interfacing device according to a second preferred embodiment of the present invention is shown in FIGS. 14A to 15B. The home biodata interfacing device shown therein includes, in addition to the service console 1 including the lid 11, a plurality of measurement instruments and an instruments canister. The measurement instruments shown therein includes an operating switch 30, a sphygmomanometer 31, a clinical thermometer 32 and a blood-sugar tester 33, and the instrument canister includes an in-box tray 34.

The measurement instruments 31,32 and 33 and the in-box tray 34 are shown in FIG. 14B in a fashion separated from each other, but without making it difficult to see where they should be in relation to the service console 1. As shown in FIGS. 14A and 14B, the in-box tray 34 is separable from the service console 1 and is designed to be snugly and neatly accommodated within the service console 1.

When the home biodata interfacing device of the type utilizing the in-box tray 34 as shown in FIGS. 14A and 14B is in use, all of the measurement instruments 31, 32 and 33 can be removed from the service console 1 at a time if while the lid 11 is in the opened position the user removes the in-box tray 34 and places it by the service console 1 as shown in FIG. 14C. Since the measurement instruments 31, 32 and 33 removed together with the in-box tray 34 are arranged neatly, use thereof is indeed convenient. After a measurement, they can be stored together with the in-box tray 34 neatly within the service console 1.

According to this embodiment, it is possible to provide the home biodata interfacing device of the structure in which the measurement instruments 31, 32 and 33 are neatly accommodated within the service console 1 and the display unit 12 is installed on the outer surface of the lid 11 and, also, in which the measurement instruments 31, 32 and 33 can readily and smoothly be removed from the service console 1 and, even after they have been removed from the service console 1, they can be kept neatly arranged within the in-box tray 34, and which is hence compact in structure, easy to handle and convenient to use.

In describing the foregoing embodiment, although the measurement instruments have been enumerated as including the sphygmomanometer 31, the thermometer 32 and the blood-sugar tester 33, any measurement instruments other than those referred to above may be employed, provided they can be used to collect biodata from the patient, together with or independent from various related accessories.

Also, the instrument canister has been used in the form of the in-box tray 34. However, the instrument canster may not always be limited to the in-box tray 34, but any instrument canster may be employed provided that it is of a shape and a configuration that can be accommodated within the service console 1 and that can accommodate the measurement instruments. By way of example, the in-box tray 34 may be a mesh tray (a tray molded from a plastic or metallic mesh sheet) or a wire-netted or frame-structured tray.

FIGS. 15A and 15B illustrate another example of the instrument canister which is in the form of an in-box tray 35 having its bottom panel formed with a plurality of, for example, three pockets each contoured generally to an outer perimeter of the corresponding measurement instrument, that is, the sphygmomanometer 31, the thermometer 32 or the blood-sugar tester 33, and hence configured to receive it snugly. As clearly shown in FIG. 15B, pockets 35a and 35b are used to receive therein the sphygmomanometer 31 including the cuff thereof, the pocket 35c is used to receive therein the thermometer 32, and pockets 35d and 35e are used to receive therein the blood-sugar tester 33 and a related component part.

The home biodata interfacing device utilizing the in-box tray 35 shown in FIGS. 15A and 15B while having advantages substantially identical to those exhibited by the previously described embodiment has an additional advantage in that the measurement instruments 31, 32 and 33 do not move and/or roll arbitrarily during transportation of the home biodata interfacing device as they are caught within the pockets 35a to 35e. Accordingly, even though the home biodata interfacing device is somewhat roughly handled during transportation, there is no possibility of some or all of the measurement instruments within the service console 1 colliding against each other.

Formation of the pockets in the bottom of the in-box tray 35 brings about further advantages. Specifically, emptiness of one or some of the pockets 35a to 35e provides a visual indication that the corresponding measurement instrument has not yet been stored. Also, emptiness of one or some of the pockets 35a to 35e in combination with the shape or contour of such one or some of the pockets 35a to 35e provides a visual indication of which one or some of the measurement instruments that fit into such one or some of the pockets 35a to 35e have not yet been stored. Accordingly, the user's failure to store one or some of the measurement instruments after the use thereof can advantageously be avoided, with no possibility of one or some of the measurement instruments being left behind at a place where the home biodata interfacing device has been transported for measurement at such place.

A further example of the instrument canister is shown in FIG. 16. The instrument canister shown in FIG. 16 includes two in-box trays 35 and 36 adapted to be accommodated within the service console 1 one at a time. The in-box tray 35 shown therein is substantially identical with that shown in FIGS. 15A and 15B and is used to accommodate the sphygmomanometer 31, the thermometer 32 and the blood-sugar tester 33, whereas the in-box tray 36 is substantially similar in structure to the in-box tray 35, but is used to accommodate a blood oxygen saturation tester 37, a clinical thermometer 32 and a urine assay kit 38.

It is to be noted that in FIG. 16, the in-box trays 35 and 36 are shown as if positioned in side-by-side relation relative to each other with respect to the service console 1. It is for the purpose of showing that since the in-box trays 35 and 36 are of the same size, either one of them can be accommodated within the service console 1 at a time. In other words, depending on the particulars of measurement desired to be performed, one of the in-box trays 35 and 36 with the corresponding measurement instruments accommodated therein can be used in the service console 1 in place of the other of the in-box trays. In the illustrated example, the in-box tray 35 is used where the patient for which the home biodata interfacing device is used requires the use of the sphygmomanometer 31, the thermometer 32 and the blood-sugar tester 33, whereas the in-box tray 36 is used where the patient requires the use of the blood oxygen saturation tester 37, the thermometer 32 and the urine assay kit 38.

For example, in a hospital where patients suffering different diseases are hospitalized, a combination of the service console 1 with the in-box tray 35 may be used for a patient of a particular disease, whereas a combination of the service console 1 with the in-box tray 36 may be used for a different patient of a different disease. Thus, if various combinations of the measurement instruments are made readily available together with corresponding in-box trays, and if depending on the particular case one of those combinations together with the respective in-box tray is chosen, the single service console 1 can be used to suit a different situation, and in this sense the home biodata interfacing device of the present invention has a relatively large range of flexibility in use.

Moreover, even though new medical instruments are invented and put into practical use, replacement of the existing in-box tray with a newly designed in-box tray effective to accommodate new medical instruments is sufficient for a single service console 1 to be utilizable in combination therewith. Thus, the present invention is indeed promising. As such, the number of the in-box trays to be reserved may not be limited to two such as shown, but may be more than two.

Figure 17A:
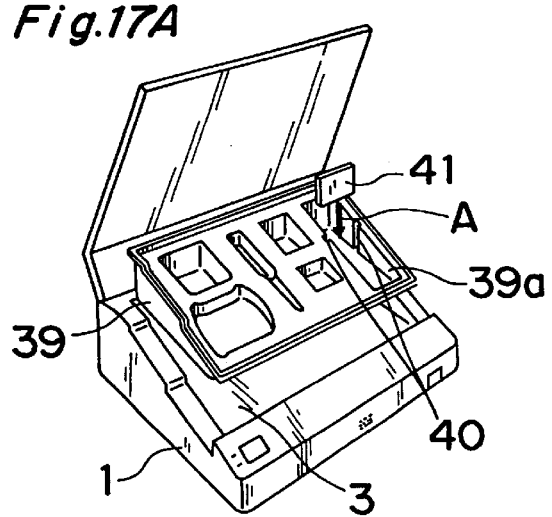
FIG. 17A is a schematic perspective view of the home biodata interfacing device according to a third modification of the second embodiment, with the in-box tray shown as floated above the service console.
Figure 17B:
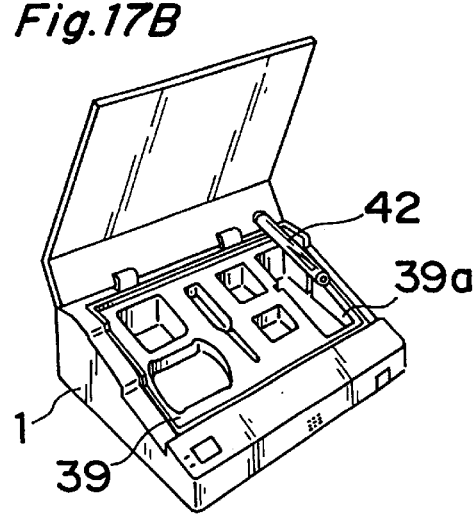
FIG. 17B is a view similar to FIG. 17A, showing the in-box tray as nested within the service console.
Figure 17C:
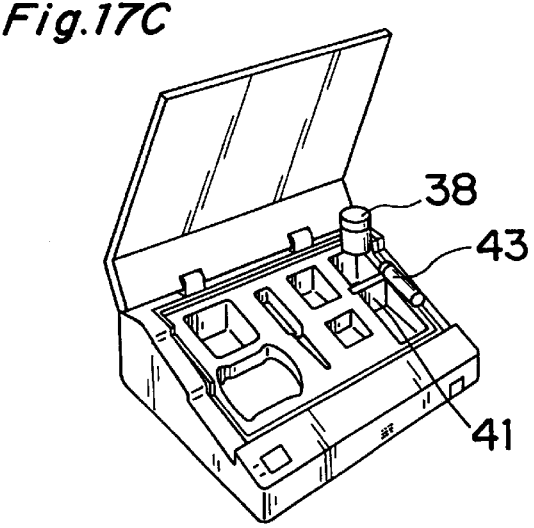
FIG. 17C is a view similar to FIG. 17B, showing a urine assay kit accommodated in a pocket which has been occupied by a penlight in FIG. 17B.

In a modification shown in FIGS. 17A to 17C, while the home biodata interfacing device shown therein is substantially similar to that shown in FIG. 16, an in-box tray 39 different from the in-box trays shown in FIG. 16 is employed and adapted to be accommodated within the attachment storage compartment 3 in the service console 1. The in-box tray 39 differs from the in-box tray or trays shown in FIG. 16 in that as clearly shown in FIGS. 17A to 17C, opposite walls of pocket 39a are formed with respective grooves 40 so as to extend in a direction conforming to the depth of the pocket 39a for accommodating a partition plate 41 that divides the pocket 39a into two rooms with opposite side edges of the partition plate 41 received in the respective grooves 40.

Where no partition plate 41 is used as shown in FIG. 17B, an elongated instrument such as, for example, a penlight 42 can be accommodated within the pocket 39a. In this condition, the penlight 42 can be substantially snugly accommodated within the pocket 39a and, therefore, will not move or roll arbitrarily. Where no penlight 42 is called for and, instead, a urine assay kit 38 and its related accessory are required, the partition plate 41 may be used to define the two rooms in the pocket 39a for accommodating the assay kit 38 and the accessory, respectively. As such, there is no possibility that measurement instruments within the in-box tray 39 will become disordered.

According to the modification shown in FIGS. 17A to 17C, the capability of the pocket 39a being divided into the two rooms is effective and advantageous in that even though a necessity arises to accommodate different measurement instruments and their related accessories, the pocket 39a can accommodate them. The in-box tray 39 of this design does not result in increase of cost and is flexible in that different measurement instruments can be accommodated one or two at a time.

While in describing the modification shown in FIGS. 17A to 17C it has been described that only one pair of the opposite grooves 40 are used only in one pocket, that is, the pocket 39a, the pair of the opposite grooves 40 may be used in all of the pockets and/or a plurality of pairs of the opposite grooves 40 may be equally used in one or all of the pockets. In addition, as partitioning structure, instead of the partition plate, a partitioning net or a rod, if it serves a partitioning purpose, can be equally employed.

Figure 18A:
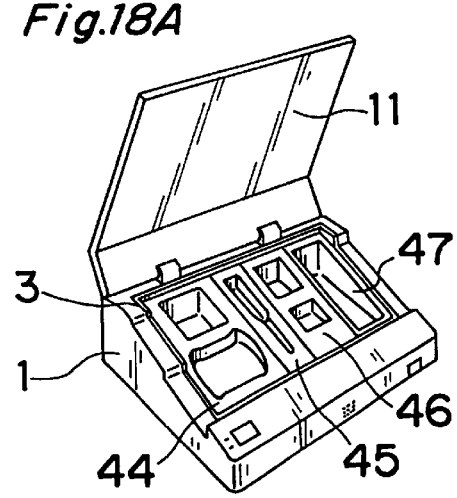
FIGS. 18A to 18C are views similar to FIGS. 17A to 17C, respectively, showing a fourth modification of the second embodiment of the present invention.
Figure 18C:
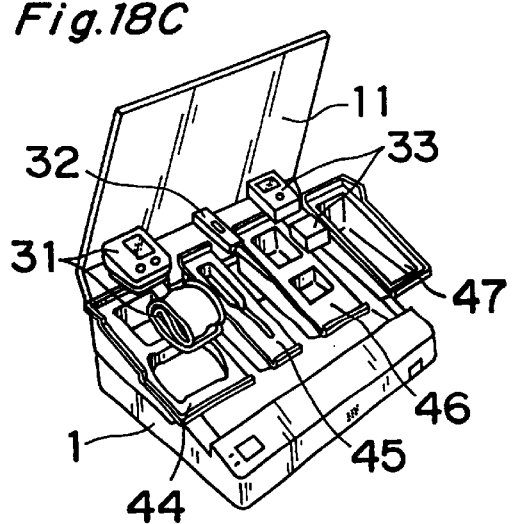
Figure 18B:
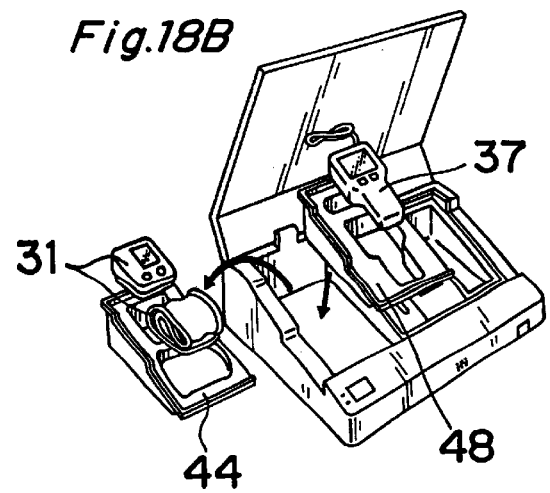

FIGS. 18A to 18C illustrate a further modification of the home biodata interfacing device. The home biodata interfacing device shown therein makes use of an instrument canister including a plurality of, for example, four separate in-box trays 44, 45, 46 and 47, all of which can be neatly accommodated within the attachment compartment 3 in the service console 1 in a manner as shown in FIG. 18A. The in-box trays 44 to 47 may have their pockets configured to accommodate specific shapes of the measurement instruments. For example, the in-box tray 44 is for accommodating the sphygmomanometer 31 and the cuff; the in-box tray 45 is for accommodating the thermometer; the in-box tray 46 is for accommodating the blood-sugar tester 33; and the in-box tray 47 is for accommodating miscellaneous accessories although a measurement instrument that may be needed may be accommodated therein.

The modification shown in FIGS. 18A to 18C is particularly advantageous in that as best shown in FIG. 18C, when the user does not intend to use, for example, the sphygmomanometer 31, but to use the blood oxygen saturation tester 37, the in-box tray 44 accommodating the sphygmomanometer 31 can be replaced with a new in-box tray 38 designed to suit to blood oxygen saturation tester 37. Similarly, even when an old-fashioned sphygmomanometer 31 is desired to be replaced with a newly developed sophisticated sphygmomanometer of a compact size, this new model can be accommodated merely by replacing the in-box tray for the old instrument 31 with a new in-box tray designed to accommodate the new instrument.

In addition, if all of the in-box trays 44 to 47 have an equal width, the user can select a desired combination of those in-box trays as he or she desires. These separate in-box trays 44 to 47 may be connected side-by-side by the use of any suitable fastening elements and, all of the in-box trays 44 to 47 can be removed at the same time from the service console 1.

According to the modification shown in FIGS. 18A to 18C, in addition to advantages and effects similar to those described hereinabove, an additional advantage can be appreciated in that one or some of the in-box trays 44 to 47 can be replaced with a new one or ones at a minimal replacement cost. Where, for example, one of the measurement instruments that was initially accommodated together with the in-box trays in a particular home biodata interfacing device is old-fashioned and a new model of a different size comes to be marketed, replacement of the respective in-box tray with a new in-box tray designed to accommodate the new model would be sufficient and, therefore, the home biodata interfacing device can be "updated" merely by such replacement. Even this replacement cost would be minimal.

It is to be noted that although in the foregoing modification the separate in-box trays are used one for each measurement instrument, each of the separate in-box trays may be designed to accommodate two or more measurement instruments.

Figure 19:
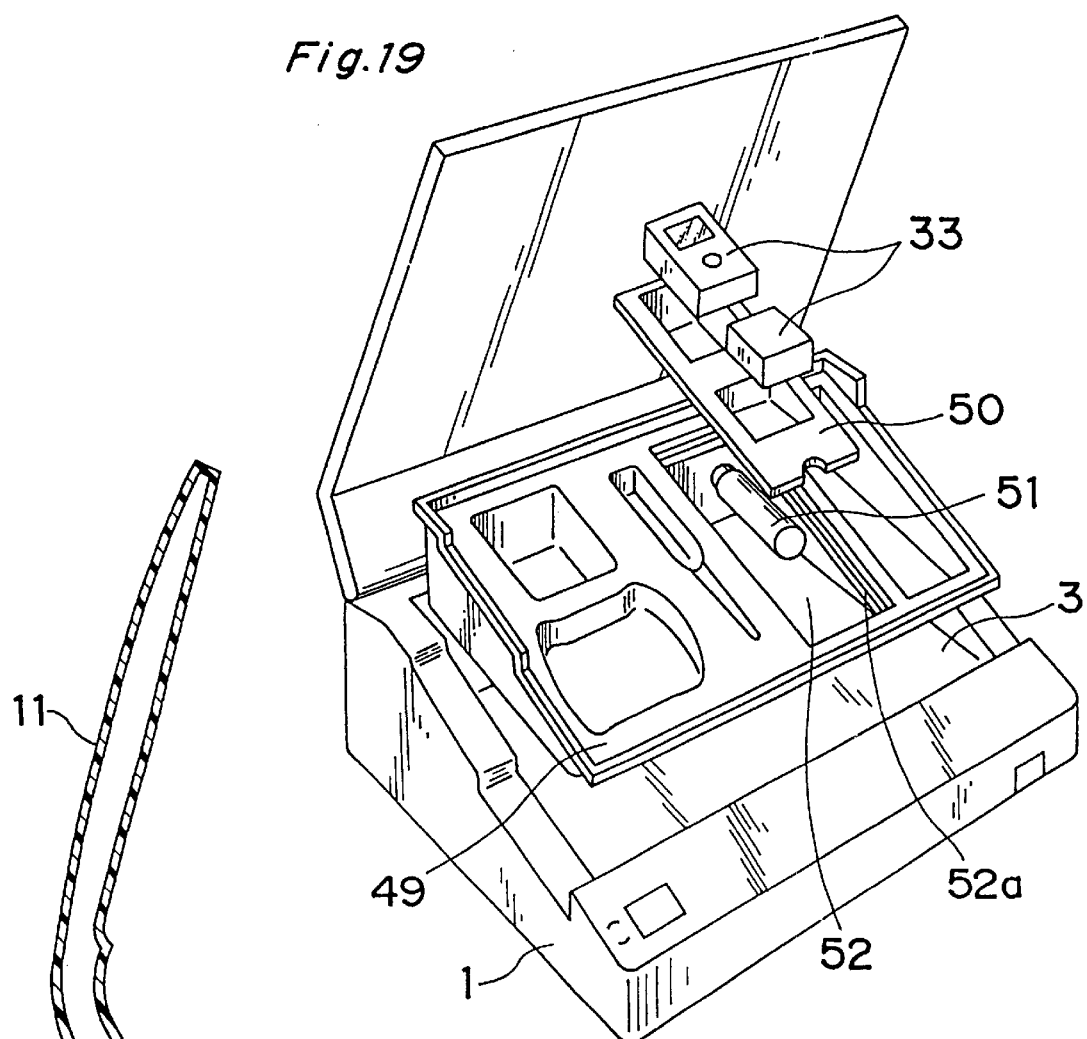
FIG. 19 is a schematic perspective view of the home biodata interfacing device according to a fifth modification of the second embodiment.

A modified form of in-box tray shown generally by 49 in FIG. 19 has a plurality of pockets similar to those described hereinbefore, one of which is shown by 52. This in-box tray 49 additionally includes a combined lid and tray 50 adapted to be capped onto the pocket 52 to close the opening of the pocket 50. The combined lid and tray 50 has one or more, for example, two, pockets defined therein for accommodating the blood-sugar tester 33. When this combined lid and tray 50 is capped onto the pocket 52 a chamber is left between the bottom of the combined lid and tray 50 and the bottom of the pocket 52 for accommodating, for example, a medicine container 51.

In order for the combined lid and tray 50 to be capped onto the pocket 52, a peripheral lip region of the opening of the pocket 52 is inwardly stepped at 52a to define a support shoulder for support of the combined lid and tray 50 when the latter is capped onto the pocket 52. The support shoulder 52a is preferably so positioned as to permit the combined lid and tray 50, when it is capped onto the pocket 52, to be held substantially flush with an upper surface of the in-box tray 49. It is to be noted that in place of the support shoulder 52a, four corner legs may be employed of a length smaller than the depth of the pocket 52 or that the combined lid and tray 50 may have a gull-wing flange that rests on the upper surface of the in-box tray 49 when it is mounted onto the pocket 52. In any event, any support system such as a friction support system may be employed provided that the "double-decker pocket" design such as envisioned in the modification shown in FIG. 19 can be realized.

One or all of the remaining pockets in the in-box tray 49 may be similarly designed to have a respective combined lid and tray. In any event, the "double-decker pocket" design is effective to maximize efficiency of utilization of space available in the in-box tray 49.

Figure 20:
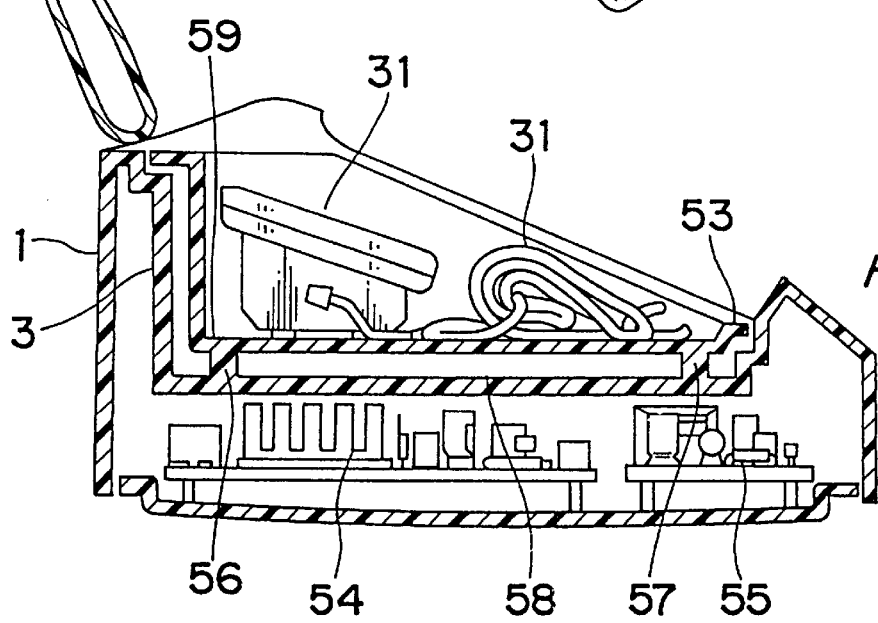
FIG. 20 is a schematic side sectional view of the home biodata interfacing device according to a sixth modification of the second embodiment.

Referring to FIG. 20, there is shown a modified form of the home biodata interfacing device. As shown therein, the service console 1 has an attachment storage compartment 3 in which an in-box tray 53 as the instrument canister is accommodated. A measurement instrument, for example, a sphygmomanometer 31 is encased within the in-box tray 53. Electronic circuits 54 and 55 for activating the home biodata interfacing device are housed within the service console 1.

According to the structure shown in FIG. 20, the sphygmomanometer 31 has no way of contacting the wall defining the attachment storage compartment 3 and is accommodated therein by way of the in-box tray 53. This in-box tray 53 has a plurality of corner legs 56 and 57 protruding outwardly from a bottom wall 59 thereof, which corner legs 56 and 57 rest on a bottom 58 of the attachment storage compartment 3 when it is accommodated within the service console 1. A space defined by the corner legs 56 and 57 between the bottom wall 59 of the in-box tray 53 and the bottom 58 of the attachment storage compartment 3 serves as an adiabatic space by which transmission of heat produced by the electronic circuits 54 and 55 and conveyed to the interior of the in-box tray 53 can advantageously be minimized. Accordingly, any possible temperature-dependent change in characteristics of the measurement instruments which would otherwise occur if a large quantity of heat is transmitted from the electronic circuits 54 and 55 and conveyed to the interior of the in-box tray 53 can be minimized or substantially eliminated. Considering that the measurement instruments are precision instruments, this is particularly important.

It is to be noted that although as structure for defining the adiabatic space the corner legs 56 and 57 have been employed, any spacer structure may be employed such as, for example, a gull-wing flange with which the in-box tray 53 can be hung from a peripheral lip region of the top opening of the service console 1.

In a still further modification shown in FIG. 21, an in-box tray 60 for accommodating measurement instruments is provided with handles 61 to facilitate an easy removal of the in-box tray 60 from the attachment storage compartment 3 in the service console 1. Thus, the use of the handles 61 should be very convenient for a user such as an aged person having a weak grip or a user who is not good at delicate handicraft.

Although the handles 61 are each shown as a channel-shaped rod, they may be constituted by finger holes, grip projections or any other elements that can be gripped by the user.

In a still further preferred embodiment of the present invention shown in, for example, FIGS. 22A to 22F, the service console 1 is designed to accommodate two different in-box trays 62 and 63 one at a time. So far described, this design is similar to that described with reference to FIG. 16 and the in-box trays 62 and 63 can be selected one at a time for use in the service console 1 depending on the type of measurement desired to be performed. However, the design shown in FIGS. 22A to 22F differs from that shown in FIG. 16 in that the different in-box trays 62 and 63 are provided with a respective identifier and the service console 1 is provided with a common identifier reader.

Specifically, while the identifier reader employed in the service console 1 is shown as used in the form of a push-button switch 65, the identifier provided in one of the in-box trays, for example, the in-box tray 63 is employed in the form of an actuating tongue 64 formed integrally with the in-box tray 63 so as to protrude laterally outwardly therefrom and positioned at such a location where, when the in-box tray 63 is accommodated within the attachment storage compartment 3 in the service console 1, the actuating tongue 64 can depress the push-button switch 65 to activate the latter. The identifier in the other in-box tray 62 is represented by a void and null so that the push-button switch 65 will not be activated.

Figure 22A:
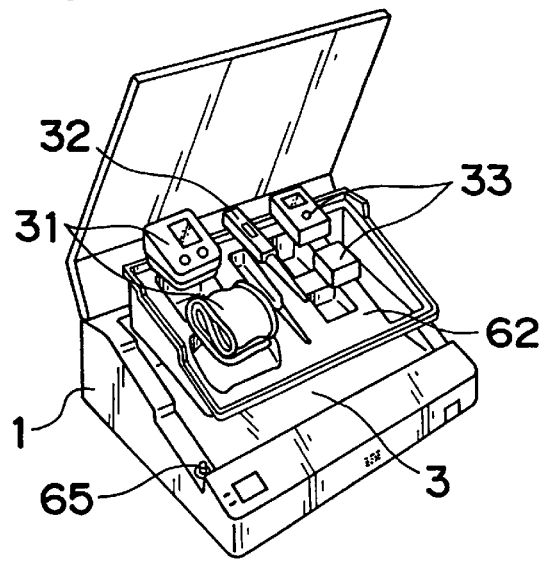
FIGS. 22A to 22C are schematic perspective views of the home biodata interfacing device according to a seventh modification of the second embodiment.
Figure 22D:
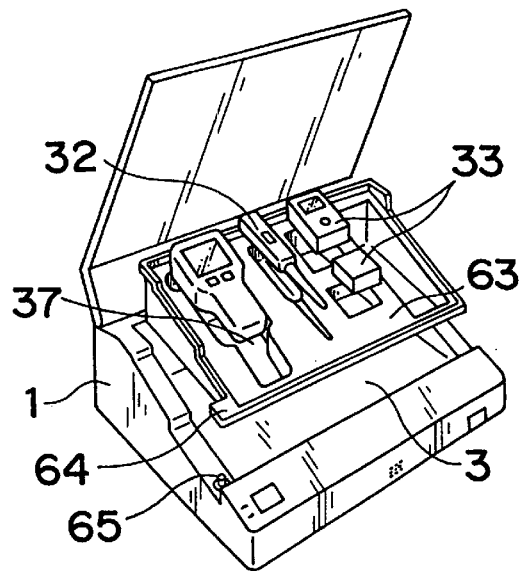
FIGS. 22D to 22F are views similar to FIGS. 22A to 22C, respectively, showing the home biodata interfacing device according to an eighth modification of the second embodiment.
Figure 22B:
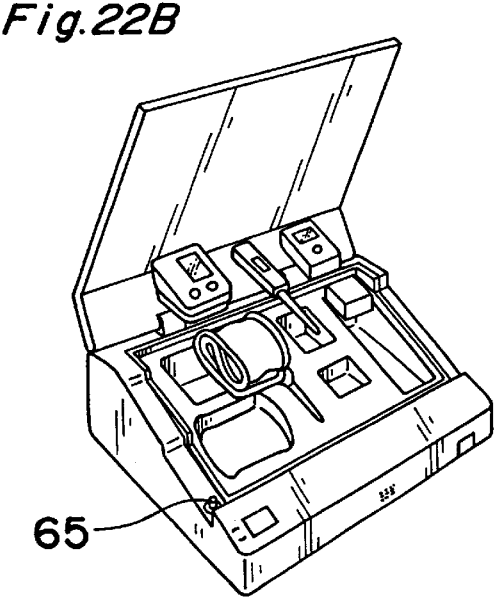
Figure 22E:
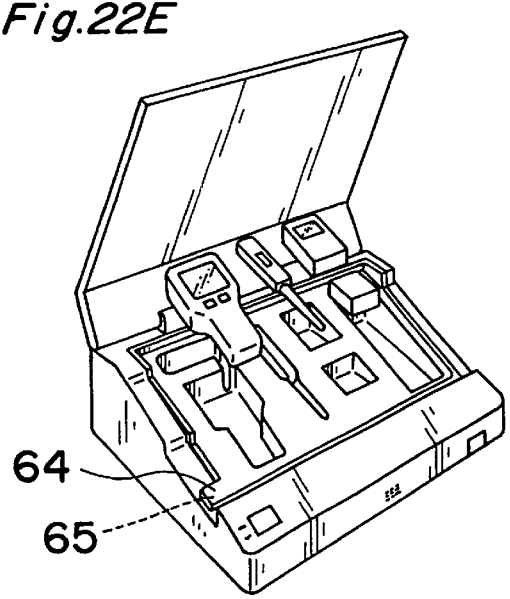
Figure 22C:
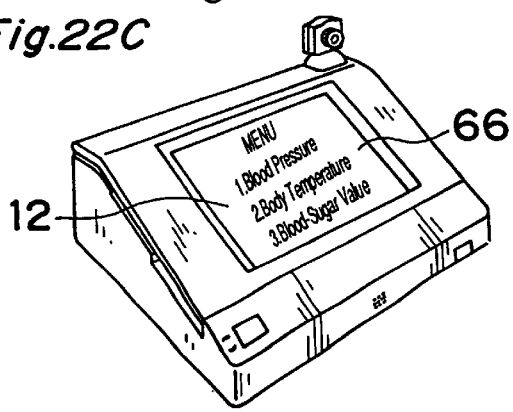
Figure 22F:
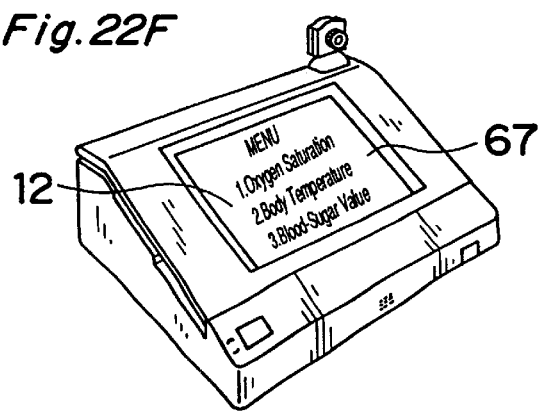

Thus, when the in-box tray 62 is used as shown in FIGS. 22A to 22C, the push-button switch 65 will not be activated, but when the in-box tray 63 is used as shown in FIGS. 22D to 22F, the push-button switch 65 will be activated. Depending on whether the push-button switch 65 has been activated, the user can know which one of the in-box trays 62 and 63 is accommodated within the attachment storage compartment 3 in the service console 1 in a manner as will become clear from the description that follows.

An electronic circuit configuration employed in the home biodata interfacing device in association with the display unit 12 is such that when, and so long as, the in-box tray 62 is used within the attachment storage compartment 3, the push-button switch 65 remains inactivated and, therefore, a display window 66 bearing such legends as "Blood Pressure", "Body Temperature" and "Blood-sugar Value" can be displayed on the display panel 12 as best shown in FIG. 22C. On the other hand, when, and so long as the in-box tray 63 is used within the attachment storage compartment 3, the push-button switch 65 is activated via contact with the actuating tongue 64 and, therefore, a display window 67 bearing such legends as "Oxygen Saturation", "Body Temperature" and "Blood-sugar Value" can be displayed on the display panel 12 as best shown in FIG. 22F.

As described above, according to the modification shown in FIGS. 22A to 22F, depending on whether the push-button switch 65 remains inactivated or activated, the different display windows 66 and 67 can be displayed one at a time to provide a visual indication of one of the in-box trays 62 and 63 then accommodated within the attachment storage compartment 3. For example, when it occurs that after the home biodata interfacing device has been used by a certain user, a different user attempts to use the same home biodata interfacing device, and if the different in-box trays such as those designated by 62 and 63 are dedicated to those different users, respectively, modes of operation of the home biodata interfacing device can be automatically switched in response to placement of either one of those in-box trays into the service console 1 to suit the particular user's requirement.

In the embodiment described above, the actuating tongue 64 and the push-button switch 65 have been used as the identifier and the reader, respectively. However, an optical reading system including a bar-code array and a bar-code reader or an induction reading system including a coil and a resonant circuit may be employed in place of a combination of the actuating tongue 64 and the push-button switch 65. Also, the number of combinations of the identifier with the reader may not be limited to one such as described above, but a plurality of the identifier-reader combinations may be employed, for example, where plural in-box trays are used in a single service console 1 such as shown in FIGS. 18A to 18C.

Furthermore, it may occur that different users may use, in association with the single service console 1, the respective in-box trays of the same shape and configuration having the same measurement instruments one at a time, and accordingly an idea of switching the modes of operation each unique for the particular user under such circumstances in response to placement of one of those in-box trays that is selected by the particular user should be understood as included within the scope of the present invention. To accomplish this, an override software program by which the single service console 1 can have its electric circuit structure configured to suit to the particular mode of operation required by the particular user in response to placement of his or her unique in-box tray may be incorporated into the service console 1. The use of the override software program in the single service console 1 is effective in that no different software programs are needed one for each in-box tray, and this should be convenient to not only the user, but also the health care provider.

In a third preferred embodiment of the present invention, the home biodata interfacing device is provided with a TV or video camera unit 68 mounted detachably on the display support frame 13 as shown in FIG. 23. The video camera unit 68 includes a camera cable 69 extending outwardly therefrom and connected with the service console 1. The service console 1 includes a control unit 1A disposed in a bottom region of the attachment storage compartment 3.

The camera unit 68 can be used in the following manner. When a patient or user desires to collect biodata on patient's or user's health conditions, he or she opens the lid 11 and removes measurement instruments accommodated within the service console 1 for the measurement. After the measurement, the patient or user connects the connection cable 6 with the service console 1 by inserting a connection plug 7 into an information receiving port 7A. With this connection, the biodata measured by sensors 2 can be transmitted to the service console 1. Thereafter, in a manner similar to that described above, a telephone cable 10 leading from the service console 1 has to be connected with the public telephone system so that the biodata can be transmitted to a health care provider. Video images captured by the camera unit 68 are similarly transmitted over the public telephone system to the health care provider when transmission switch 4 is manipulated.

So far as the camera unit 68 is mounted on the display support frame 13, the video image captured thereby will be an image of the scene surrounding the camera unit 68 including, for example, an image of the face of the patient or user. On the other hand, if the camera unit 68 is removed from the display support frame 13 and is brought close towards an affected region of the patient, a partial image of the affected region can be transmitted. Where the patient is lying in bed, a nurse has to direct the camera unit 68 towards the lying patient so that various images including those of a complexion and/or an affected region of the patient can be transmitted over the public telephone system.

Accordingly, since the camera unit 68 connected with the service console 1 is detachably mounted on the display support frame 13, not only can the biodata outputted by the sensors 2 be transmitted to the health care provider, but a whole image of the complexion of the patient, a partial image of the affected region of the patient and/or an image of the lying patient can also be transmitted simultaneously to the health care provider if the camera unit 68 is removed from the display support frame 13, so that an assured remote diagnosis of the health conditions of the patient can be achieved.

Figure 24:
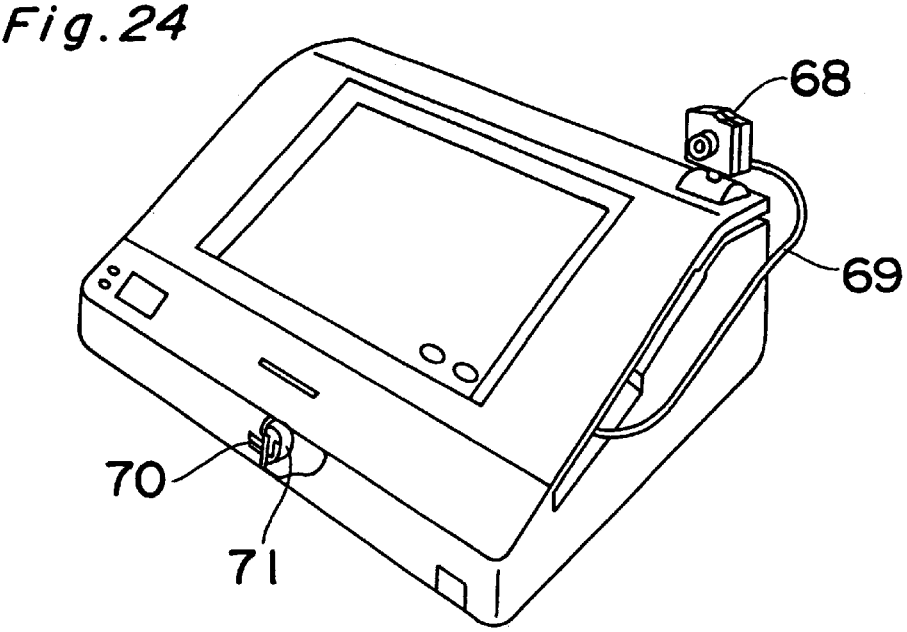
FIG. 24 is a schematic perspective view of the home biodata interfacing device shown in FIG. 23, showing a first modification of the third embodiment.
Figure 25:
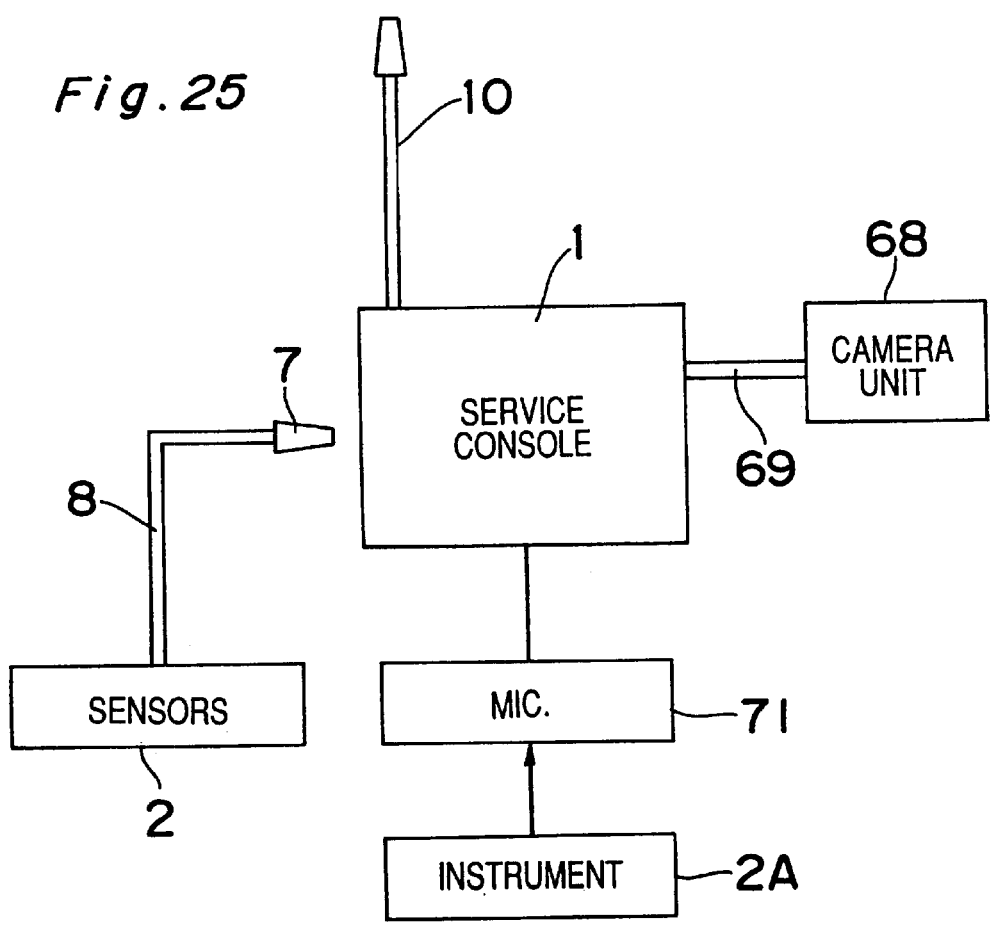
FIG. 25 is a block diagram showing a circuit structure employed in the home biodata interfacing device embodying the present invention.
Figure 26:
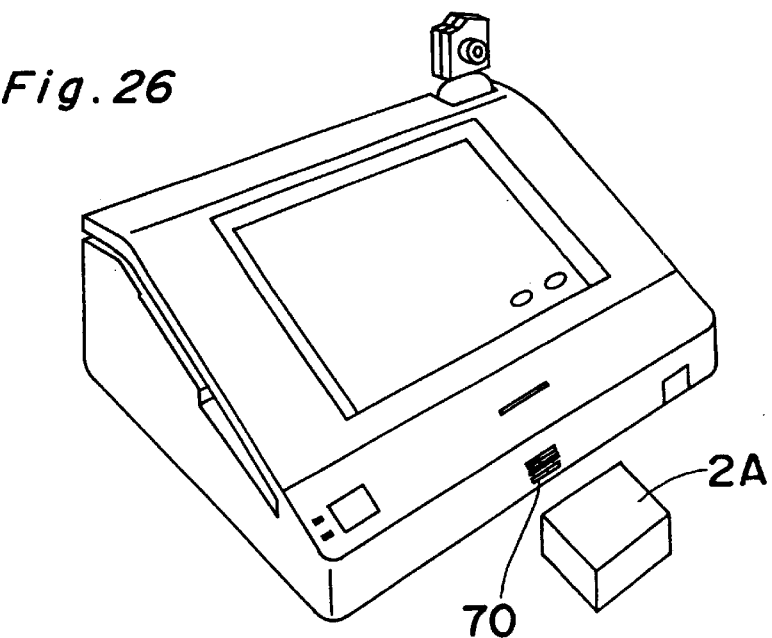
FIG. 26 is a schematic perspective view of the home biodata interfacing device, showing a second modification of the third embodiment.

As shown in FIGS. 24 to 26, a microphone port 70 may be formed in a front wall of the service console 1 with a microphone 71 disposed behind such microphone port 70. Where the microphone 71 is employed, voiced messages spoken by the patient and/or the nurse and/or a voice signal generated from a measuring instrument 2A for generating such voice signal that is installed forwardly of the microphone port 70 can, after having been sensed by the microphone 71, transmitted over the public telephone system to the health care provider at a remote location. Thus, the biodata measured by the sensors 2, the video image captured by the camera unit 68 and the voice-based health care information can all be transmitted to the health care provider and, therefore, information required by a doctor going to make a diagnosis can be transmitted to the doctor to facilitate a diagnosis as accurate as possible at the remote location.

Since the microphone 71 is positioned forwardly of the service console 1, not only is it possible to receive voiced messages spoken while the service console 1 is being handled, for bidirectional communication with a doctor, but the use of the single microphone 71 is sufficient to transmit both the spoken messages and the signals from the measuring instrument 2A.

Figure 27:
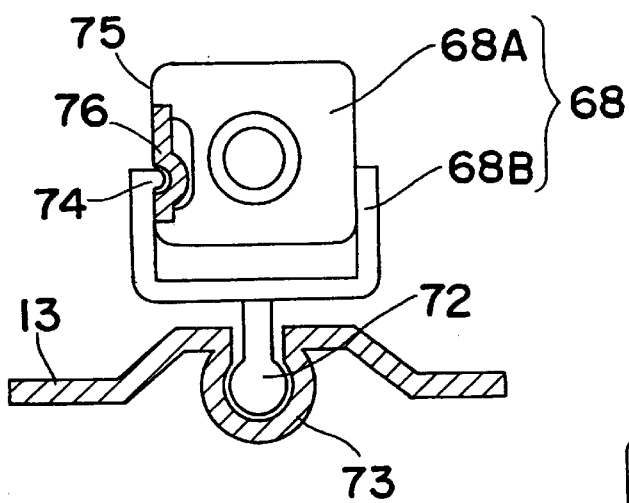
FIG. 27 is a schematic front sectional view showing a camera unit used on the home biodata interfacing device, showing a third modification of the third embodiment.
Figure 28:
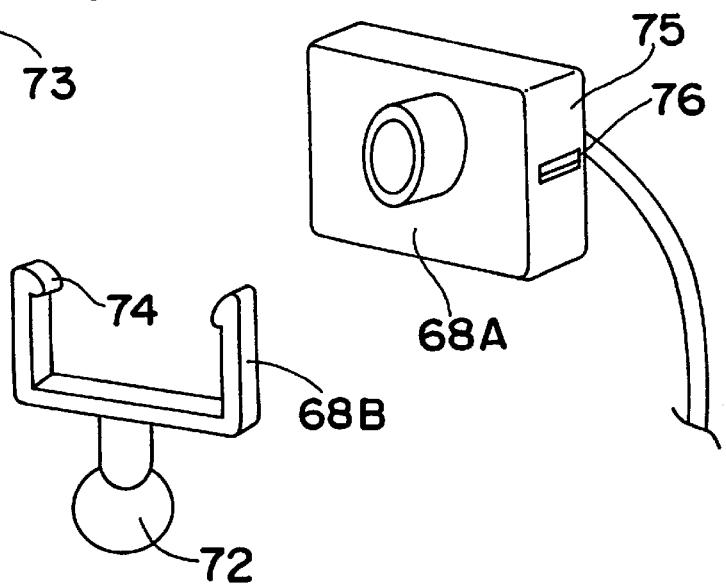
FIG. 28 is a schematic exploded view of the camera unit shown in FIG. 27.

FIGS. 27 and 28 illustrate a camera mount system. This illustrated camera mount system differs from that shown in FIG. 23 in that in this modification the camera unit 68 includes a camera body 68A detachably mounted on a camera support bracket 68B which is in turn pivotally mounted on the display support frame 13 by virtue of a ball member 72 that forms a part of the camera support bracket 68B. The display support frame 13 has a spherically recessed bearing pocket 73 within which the ball member 72 is accommodated for pivotal movement in all directions.

In this camera mount system, as the ball member 72 moves frictionally freely within the bearing pocket 73, the camera unit 68 can be pivoted about a center of the ball member 72. Accordingly, there is no need to move or rotate the service console 1 and merely by tuning the camera unit 68 in any desired direction, video images of a required zone of the patient captured at any desired angle can be transmitted over the public telephone system.

As best shown in FIG. 28, the camera support bracket 68B is made up of a generally U-shaped frame and a portion of the bracket 68B corresponding to a base of the U shape is provided with the ball member 72 through a downwardly extending leg. Opposite free end portions of the support bracket 68B are formed with respective bearing projections 74 protruding therefrom in respective directions facing each other. On the other hand, opposite side walls of the camera body 68A are formed with respective bearing recesses 76 defined in opposite side walls 75 of the camera body 68A for receiving the corresponding bearing projections 74.

With the bearing projections 74 engaged in the associated bearing recesses 76 by the effect of resiliency exhibited by the support bracket 68B, the camera body 68A is mounted on the support bracket 68B. However, a forced pull of the camera body 68A upwardly relative to the support frame 68B results in detachment of the camera body 68A from the support frame 68B. In this way, the camera body 68A can be easily detached from or mounted onto the support bracket 68B, and video images can easily be transmitted.

Figure 29:
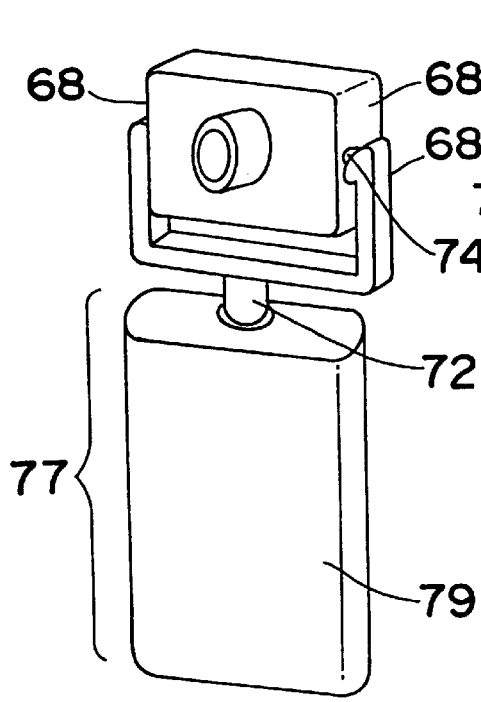
FIG. 29 is a schematic perspective view of the camera unit, showing a fourth modification of the third embodiment.
Figure 30:
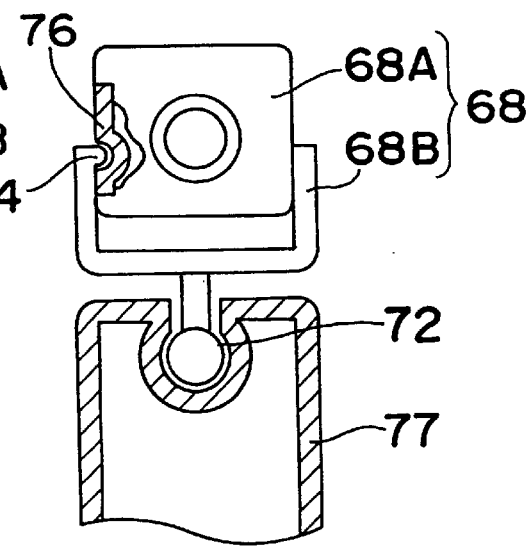
FIG. 30 is a schematic front sectional view of the camera unit shown in FIG. 29.

Even though the camera unit 68 is integrated with a holder 77 as shown in FIGS. 29 and 30, a pivot support system similar to that described in connection with FIGS. 27 and 28 can be employed so that not only can the camera body 68A be separated from the holder 77 for image capture solely with the camera body 68A, but also the holder 77 together with the camera body 68A can be detached from the service console 1. The use of the holder 77 makes it possible to allow the camera body 68A to make access to regions difficult for the camera body 68A itself to make access, thereby enabling a diversity of images to be transmitted to the health care provider.

FIGS. 29 to 32 illustrate a modified camera mount system. As shown therein, the camera body 68A is detachably mounted on the support bracket 68B, in a manner similar to that described with reference to FIGS. 27 and 28, which is in turn pivotally mounted on the holder 77 by virtue of the pivot support system also shown in FIGS. 27 and 28. It is, however, noted that in the modification shown in FIGS. 29 to 32, the ball member 72 is pivotally received in the bearing recess that is defined in the holder 77.

The holder 77 is preferably ergonomically configured to provide a good gripping sensation to the user and, in the illustrated instance, has a grip 79 defined by generally rounded sides opposite to each other.

Figure 31:
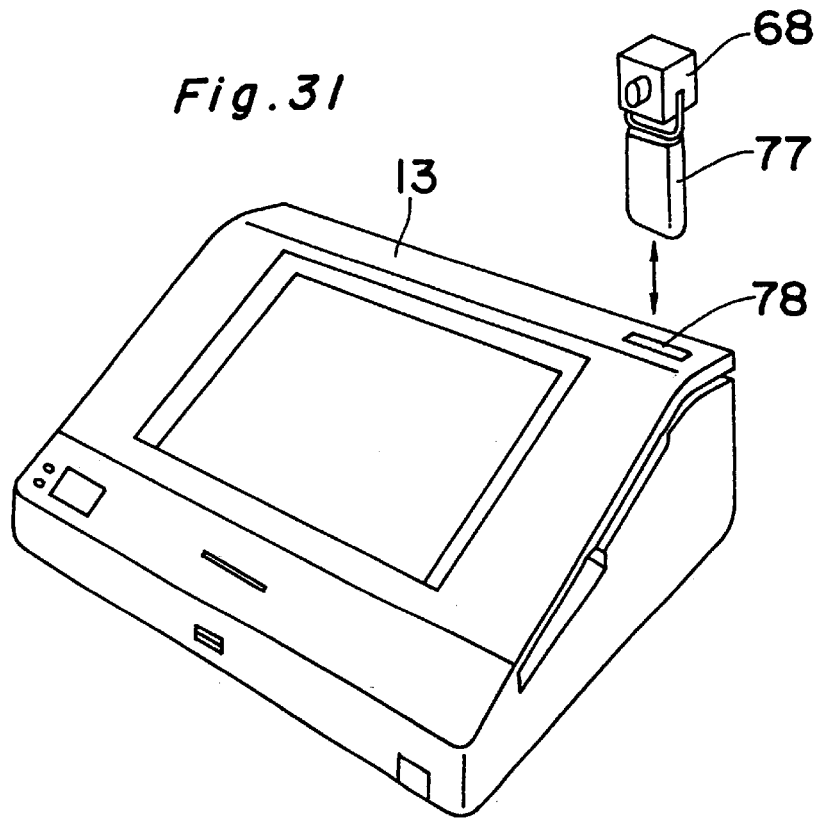
FIG. 31 is a schematic diagram showing how the camera unit of FIG. 29 is mounted on the home biodata interfacing device.
Figure 32:
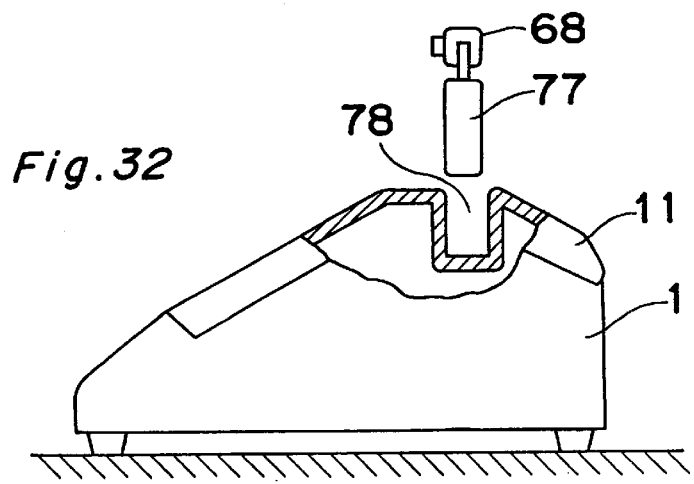
FIG. 32 is a fragmentary side sectional view of the home biodata interfacing device shown in FIG. 31.

Mounting of the assembly including the camera unit 68 and the holder 77, or of only the holder 77, onto the service console 1 can be accomplished merely by inserting the holder 77 into a holder socket 78 defined in the display support frame 13 as shown in FIGS. 31 and 32.

It is to be noted that if the grip 79 is of a generally cylindrical shape, the holder 77 can be more easily gripped and, therefore, the camera unit 68 can be more easily moved from place to place with images of required regions consequently transmitted to the health care provider more easily.

If desired, the camera body 68A itself or the camera assembly including the camera unit 68 and the holder 77 can be stored in the in-box tray 47 shown in FIGS. 18A to 18C when they are not in use. Since in such case after the camera cable 69 has been disconnected from the service console 1, the camera body 68A or the camera assembly 68 and 77 can be stored in the in-box tray 47 then accommodated within the attachment storage compartment 3, the camera unit will not provide an eyesore which would occur if it is left as mounted externally on the service console 1. In addition, with the camera body 68A or the camera assembly 68 and 77 encased inside the service console 1, closure of the lid 1 protects it from being damaged while providing an aesthetic appearance of the home biodata interfacing device as a whole.

Figure 33:
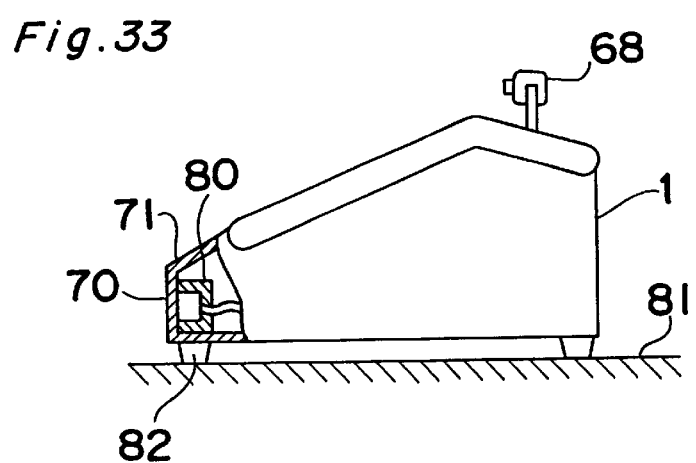
FIGS. 33 and 34 are views similar to FIG. 32, showing respective manners of supporting a microphone and a voice input measuring instrument, respectively, in the home biodata interfacing device.

FIG. 33 illustrates the manner in which the microphone 71 is installed. The microphone 71 is enclosed by an elastic material 80 which is in turn fixedly retained inside the service console 1. Support legs 82 secured to a bottom of the service console 1 for support of such service console 1 on top of a desk 81 are also made of elastic material 80.

Since the microphone 71 is enclosed by the elastic material 80, vibrations generated inside the service console 1 and/or transmitted externally thereto are cushioned by the elastic material 80 and will therefore not be transmitted to the microphone 71, allowing noiseless voice signals to be transmitted over the public telephone system. Also, since the legs 82 are made of the elastic material, the service console 1 is less sensitive to external vibrations transmitted through the desk 81.

Figure 34:
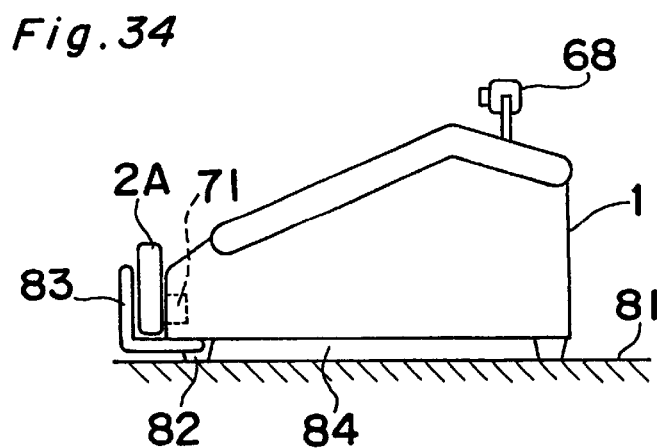

FIG. 34 illustrates the use of a generally L-shaped support member 83 secured to a bottom surface 84 of the service console 1 for retention of the voice input measuring instrument 2A in front of the microphone 71 in the service console 1.

With such a construction as shown in FIG. 34, the measuring instrument 2A can be positioned forwardly of the microphone 71 having been retained by a support member 83 and, therefore, when the voice signal from the measuring instrument 2A is to be transmitted to the service console 1, the user need not hold the measuring instrument 2A, and the measuring instrument 2A can be stably retained by the support member 83 and, accordingly, without the measuring instrument 2A being displaced from the position in front of the microphone 71, the voice signal can be transmitted with minimized noise.

Figure 35A:
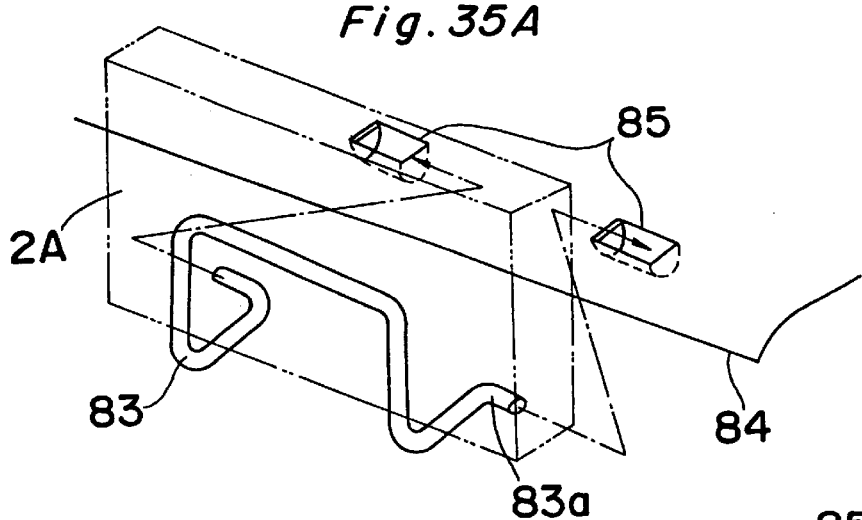
FIGS. 35A and 35B are schematic perspective views showing different support members for the voice input measuring instrument.
Figure 35B:
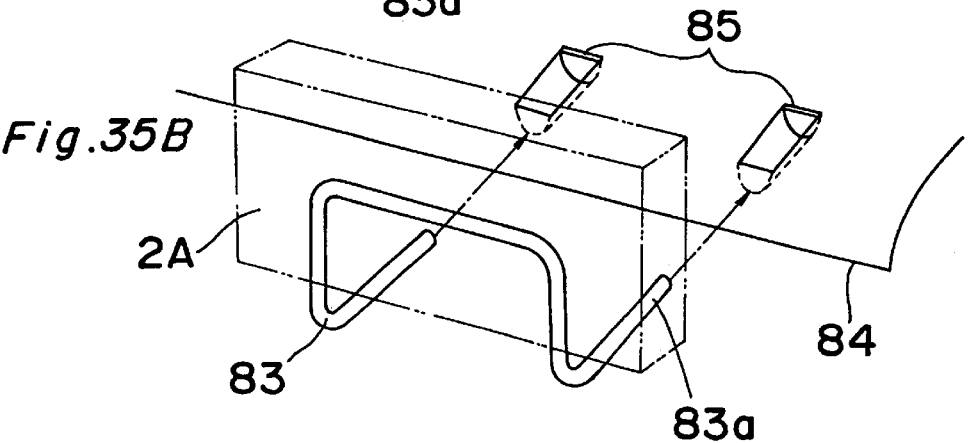

As shown in FIGS. 35A and 35B, the support member 83 is made in the form of a wire member bent to represent a generally L-shaped configuration with its opposite free ends 83a inserted into respective bearings 85 formed on the bottom surface 84 in a depressed fashion so that the support member 83 can be detachably or slidably connected to the service console 1.

In particular, where the support member 83 and the bearings 85 are constructed as shown in FIG. 35A, when the support member 83 is inserted into the bearings 85 on the bottom surface 84 of the service console 1, the voice input measuring instrument 2A can be retained by the support member 83 at a location forwardly of the service console 1 and, if the necessity arises, the support member 83 can be detached from the bearings 85.

Alternatively, where the support member 83 and the bearings 85 are constructed as shown in FIG. 35B, even where there are a number of voice input measuring instruments 2A of different sizes, any of those measuring instruments 2A can be selectively retained by the support member 83 since the latter is slidable relative to the service console 1. In either case, the voice signal can be transmitted with minimal noise.

Figure 36:
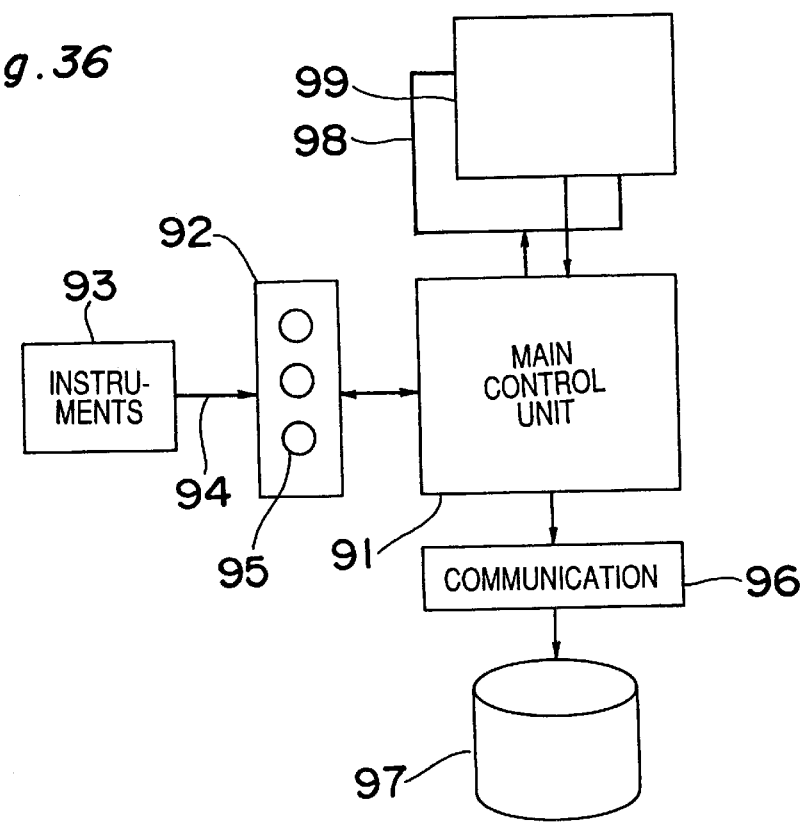
FIG. 36 is a block diagram showing a circuit structure employed in the home biodata interfacing device of the present invention.

FIG. 36 illustrates a block diagram of the home biodata interfacing device according to the present invention. Referring to FIG. 36, reference numeral 91 represents a main control unit including a central processing unit (CPU) and random access memories (RAM) for processing various information, and a loudspeaker for providing voice guidance, and reference numeral 92 represents a terminal unit having a plurality of connecting terminals 95 for receiving biodata for transfer to the main control unit. Reference numeral 93 represents medical measuring instruments which may be a body thermometer, a sphygmomanometer, and others, and outputs collected biodata through a connecting cable 94. Since at this time the connecting cable 94 and the connecting terminals 95 are electrically connected with each other, the biodata can be inputted to the main control unit 91.

The main control unit 91 is operable to convert the inputted biodata into a communication protocol according to a predetermined control rule and accumulates the data in a database 97, located at a remote place, through a communication device 96 having a modem function. The database 97 can support a plurality of home biodata interfacing devices and can manage the biodata continuously for a prolonged period of time, and a doctor using an all-purpose computer can make access to the database 97 and reviews the biodata of each of patients for diagnostic purposes.

Reference numeral 98 represents a display device, for example, a liquid crystal display device, and reference numeral 99 represents an operating panel in the form of, for example, a touch panel. The user may utilize the operating panel 99 to select one of the medical measuring instruments 93 and will initiate the measurement by connecting the connecting cable 94 to the connecting terminals 95. At this time, the manner of use of the selected medical measuring instrument 93 and the corresponding connecting terminals are provided for by virtue of image guidance using the display device.

Figure 37:
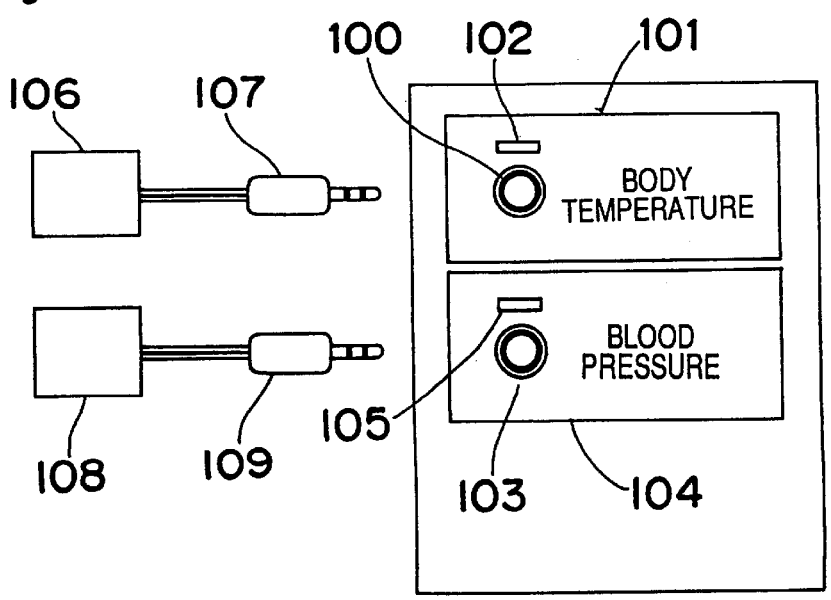
FIG. 37 is a schematic diagram showing a connection terminal unit that can be employed in the home biodata interfacing device of the present invention.

FIG. 37 illustrates an outer appearance of the terminal unit employed in the home biodata interfacing device. In this terminal unit 92, reference numeral 100 represents a thermometer connecting terminal; reference numeral 101 represents a thermometer label; reference numeral 102 represents a thermometer LED; reference numeral 103 represents a sphygmomanometer connecting terminal; reference numeral 104 represents a sphygmomanometer label; and reference numeral 105 represents a sphygmomanometer LED. The thermometer label 101 has a legend "Body Temperature" printed in a red color against a white background, whereas the sphygmomanometer label 104 has a legend "Blood Pressure" printed in a red color against a white background. On the other hand, the thermometer includes a thermometer body 106 and a thermometer connecting cable 107 colored in red, whereas the sphygmomanometer includes a sphygmomanometer body 108 and a sphygmomanometer connecting cable 109 colored in blue.

If for example, the thermometer is selected through the operating panel 99, the display device 98 displays a photo of a connection between the connecting cable 107 and the connecting terminal 100 along with a connecting method in addition to a method of measuring the body temperature. The thermometer LED 102 is also turned on and a corresponding voice guidance, "Body temperature measurement is ready. Connect the red-colored cable with the red-colored terminal.", is performed.

Figure 38:
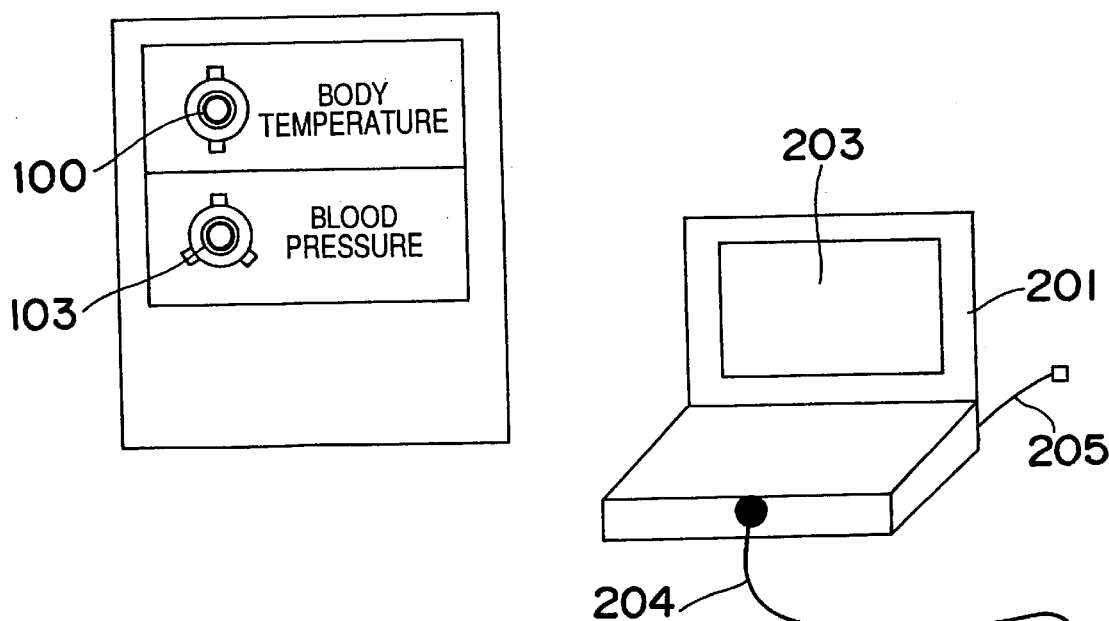
FIG. 38 shows a modified form of the connection terminal unit shown in FIG. 37.
Figure 39:
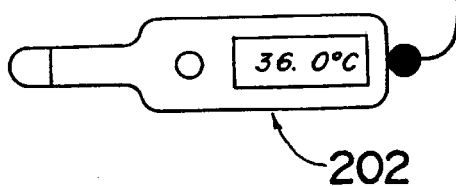
FIG. 39 is a schematic perspective view showing a prior art home biodata interfacing device.

FIG. 38 is a view similar to that shown in FIG. 37, but showing structure for avoiding an erroneous connection between a cable and a terminal. As shown therein, a portion surrounding the thermometer connecting terminal 100 is formed with two circumferentially spaced detent recesses while a portion surrounding the sphygmomanometer connecting terminal 103 is formed with three circumferentially spaced detent recesses. On the other hand, a free end of the thermometer connecting cable 107 is formed with two circumferentially spaced detent projections which, when the connecting cable 107 is plugged into the right connecting terminal, say, the terminal 100, can be received within the corresponding detent recesses. Similarly, a free end of the sphygmomanometer connecting cable 109 is formed with three circumferentially spaced detent projections which, when the connecting cable 109 is plugged into the right connecting terminal, say, the terminal 103, can be received within the corresponding detent recesses. The thermometer connecting cable 107 cannot be plugged into the terminal 103 and, similarly, the sphygmomanometer connecting cable 109 cannot be plugged into the terminal 100.

Accordingly, even though the user is unfamiliar with how to use the computer, and feels difficulty reading small legends printed or embossed adjacent the terminal unit because of far-sightedness, correct biodata can be collected and transmitted to the doctor at a remote location so that the doctor can made an accurate and correct diagnosis.

Although the present invention has been described in connection with the preferred embodiments thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A biodata interfacing device comprising:
   a service console;
   an attachment storage compartment defined in said service console for accommodating a at least one senor that are to be used for collecting biodata, said attachment storage compartment having a top opening;
   a lid mounted on said service console for movement between a first position at which said top opening of said attachment storage compartment is closed by said lid and a second position at which said top opening of said attachment storage compartment is not closed by said lid, said lid having oppositely facing upper and lower surfaces, with said lower surface facing said attachment storage compartment when said lid is at said first position; and
   a display unit on said upper surface of said lid.

2. The biodata interfacing device according to claim 1, wherein said lid is configured to be inclined downwardly towards a position of a user of the biodata interfacing device when said lid is at said first position.

3. The biodata interfacing device according to claim 2, wherein said service console includes a terminal unit through which sensors positioned externally of said service console are to communicate with said service console, said terminal unit being provided on an upper surface of said service console.

4. The biodata interfacing device according to claim 3, wherein said terminal unit is in a recess defined in an end face of said service console.

5. The biodata interfacing device according to claim 2, wherein said lid is mounted on said service console via a hinged connection about which said lid is to pivot relative to said service console.

6. The biodata interfacing device according to claim 5, wherein said hinged connection includes a damping mechanism.

7. The biodata interfacing device according to claim 6, wherein said lid has a sectional shape representing a generally hill-like shape with a vertex defined and positioned forwardly of said hinged connection, with front and rear regions of said upper surface of said lid on respective sides of said vertex being inclined downwardly from said vertex, wherein said display unit is on said front region of said upper surface of said lid.

8. The biodata interfacing device according to claim 5, wherein said lid includes a projection that is operable to interfere with said service console to limit pivotal movement of said lid before said lid is pivoted to a limit defined by said hinged connection.

9. The biodata interfacing device according to claim 5, wherein said service console includes a projection that is operable to interfere with said lid to limit pivotal movement of said lid before said lid is pivoted to a limit defined by said hinged connection.

10. The biodata interfacing device according to claim 2, further comprising an instrument canister to accommodate therein the at least one sensor, such that said instrument canister enables the at least one senor to be accommodated within said attachment storage compartment in an arrangement of the at least one sensor as accommodated within said instrument canister.

11. The biodata interfacing device according to claim 2, wherein said display unit has a surface on which is provided a touch operating panel.

12. The biodata interfacing device according to claim 2, further comprising a recess for passage therethrough of a connection line leading from the at least one sensor to exterior of the biodata interfacing device.

13. The biodata interfacing device according to claim 2, further comprising a recess in an end face of said service console for passage therethrough of connection line leading from the at least one sensor to exterior of the biodata interfacing device.

14. The biodata interfacing device according to claim 1, wherein said display unit has a surface on which is provided a touch operating panel.

15. The biodata interfacing device according to claim 1, further comprising a recess for passage therethrough of a connection line leading from the at least one sensor to exterior of the biodata interfacing device.

16. The biodata interfacing device according to claim 1, further comprising a recess in an end face of said service console for passage therethrough of a connection line, leading from the at least one senor to exterior of the biodata interfacing device.

17. The biodata interfacing device according to claim 1, further comprising an instrument canister to accommodate therein the least one senor, such that said instrument canister enables the at least one sensor to be accommodated within said attachment storage compartment in an arrangement of the variety of sensors as accommodated within said instrument canister.

18. The biodata interfacing device according to claim 17, wherein said instrument canister includes pocket defined therein of a shape corresponding to a contour of the at least one sensor so as to receive therein the at least one sensors.

19. The biodata interfacing device according to claim 17, wherein said instrument canister has a configuration corresponding to a combination of sensors for measuring data that may be necessary depending on symptoms of a user, and is replaceable by another instrument canister depending on symptoms of the user.

20. The biodata interfacing device according to claim 17, wherein said instrument canister comprises one in-box tray or plural in-box trays each corresponding to a combination of sensors for measuring data that may be necessary depending on symptoms of a user, said instrument canister being capable of being accommodated within said attachment storage compartment.

21. The biodata interfacing device according to claim 17, wherein said instrument canister includes at least one pair of grooves, and further comprising partitioning structure removably engageable within said at least one pair of grooves to change a shape of a partition room.

22. The biodata interfacing device according to claim 17, wherein said instrument canister has at least a portion thereof that is capable of being stacked in a direction heightwise thereof.

23. The biodata interfacing device according to claim 17, wherein a space is defined within said service console between said instrument canister and at least one surface that defines said attachment storage compartment for relieving heat conduction from said service console.

24. The biodata interfacing device according to claim 17, wherein said instrument canister includes a handle for facilitation of removal thereof from said attachment storage compartment.

25. The biodata interfacing device according to claim 17, wherein said instrument canister includes identifying structure for identifying a type of said instrument canister, and further comprising:

a reading device provided in said service console for reading said identifying structure; and a mode override device for changing a mode of operation of the biodata interfacing device according to a result of reading of said identifying structure by said reading device.

26. The biodata interfacing device as claimed in claim 17, further comprising:

a main control unit;

sensors for collecting biodata from a patient and converting the biodata into physical signals;

a terminal unit including connecting terminals corresponding to said sensors, respectively, and for transmitting the biodata therefrom to said main control unit; and light emitting diodes adjacent said connecting terminals, wherein said main control unit includes an operating unit and a display unit which are accessible to a user for performing manipulation, such that when the user selects one of said sensors via said operating unit, said main control unit causes said display unit to activate one of said light emitting diodes that corresponds to said one of said sensors.

27. The biodata interfacing device according to claim 26, wherein each of the said sensors comprises a sensor body and a connecting cable for electrically connecting said sensor body with a respective one of said connecting terminals, and has at least a portion thereof being of a predetermined color, and wherein said terminal unit has portions adjacent said connecting terminals that are of different colors relative to one another, with a color of one of said connecting terminals corresponding to a color of said at least a portion of a respective one of said sensors.

28. The biodata interfacing device according to claim 26, wherein said sensors have connecting cables, respectively, with said connecting cables being of different shapes relative to one another, and said connecting terminals of said terminal unit have different shapes relative to one another, with the different shapes of said connecting cables corresponding to the different shapes of said connecting terminals such that only when the shape of one of said connecting cables and the shape of one of said connecting terminals match with each other, can said one of said connecting cables and said one of said connecting terminals be electrically connected together.

29. The biodata interfacing device according to claim 17, further comprising a camera unit detachably provided on an outer surface of the biodata interfacing device.

30. The biodata interfacing device as claimed in claim 17, further comprising:

a main control unit;

sensors for collecting biodata from a patient and converting the biodata into physical signals; and a terminal unit including connecting terminals corresponding to said sensors, respectively, and for transmitting the biodata therefrom to said main control unit, wherein said main control unit includes an operating unit and a display unit which are accessible to a user for performing manipulation, such that when the user selects one of said sensors via said operating unit, said main control unit causes said display unit to provide the user with an indication of one of said connecting terminals that corresponds to said one of said sensors.

31. The biodata interfacing device as claimed in claim 1, further comprising:

a main control unit;

sensors for collecting biodata from a patient and converting the biodata into physical signals;

a terminal unit including connecting terminals corresponding to said sensors, respectively, and for transmitting the biodata therefrom to said main control unit; and light emitting diodes adjacent said connecting terminals, wherein said main control unit includes an operating unit and a display unit which are accessible to a user for performing manipulation, such that when the user selects one of said sensors via said operating unit, said main control unit causes said display unit to activate one of said light emitting diodes that corresponds to said one of said sensors.

32. The biodata interfacing device according to claim 1, further comprising a camera unit detachably provided on an outer surface of the biodata interfacing device.

33. The biodata interfacing device according to claim 32, further comprising a microphone provided in said service console.

34. The biodata interfacing device according to claim 33, wherein said microphone is capable of receiving both a human voice and a voice signal from a sensor positioned in the vicinity of said microphone.

35. The biodata interfacing device according to claim 33, wherein said microphone is enclosed by an elastic member which is fixed inside said service console.

36. The biodata interfacing device according to claim 33, further comprising a support member in front of said microphone for supporting a sensor for outputting a voice signal.

37. The biodata interfacing device according to claim 36, wherein said support member in front of said microphone is removable or slidable according to a shape of the sensor for outputting the voice signal.

38. The biodata interfacing device according to claim 32, wherein said camera unit is pivotable at a mounting area on an outer surface of said service console.

39. The biodata interfacing device according to claim 32, wherein said camera unit includes a grip by which a user can hold said camera unit when said camera unit is detached from said outer surface of the biodata interfacing device, and wherein detachment of said camera unit from the biodata interfacing device is to be carried out by removing said grip of said camera unit from engagement with said outer surface of the biodata interfacing device.

40. The biodata interfacing device according to claim 39, wherein said camera unit is pivotally engaged with said grip.

41. The biodata interfacing device according to claim 40, wherein said grip is of a generally cylindrical shape and is engageable with said outer surface of the biodata interfacing device via a recess formed in an outer surface of said service console.

42. The biodata interfacing device according to claim 39, wherein said camera unit comprises a camera body and a camera support, with said camera body being removably mounted on said camera support.

43. The biodata interfacing device according to claim 42, wherein said instrument storage compartment can accommodate therein at least one of said camera body, said camera support and said grip.

44. The biodata interfacing device as claimed in claim 1, further comprising:

a main control unit;

sensors for collecting biodata from a patient and converting the biodata into physical signals; and a terminal unit including connecting terminals corresponding to said sensors, respectively, and for transmitting the biodata therefrom to said main control unit, wherein said main control unit includes an operating unit and a display unit which are accessible to a user for performing manipulation, such that when the user selects one of said sensors via said operating unit, said main control unit causes said display unit to provide the user with an indication of one of said connecting terminals that corresponds to said one of said sensors.

45. The biodata interfacing device according to claim 44, further comprising colored indicators disposed adjacent said connecting terminals and corresponding to said connecting terminals, respectively, and wherein said main control unit has a function of informing the user via said display unit of one of said colored indicators that corresponds to a selected sensor.

46. The biodata interfacing device according to claim 44, wherein each of the said sensors comprises a sensor body and a connecting cable for electrically connecting said sensor body with a respective one of said connecting terminals, and has at least a portion thereof being of a predetermined color, and wherein said terminal unit has portions adjacent said connecting terminals that are of different colors relative to one another, with a color of one of said connecting terminals corresponding to a color of said at least a portion of a respective one of said sensors.

47. The biodata interfacing device according to claim 44, wherein said sensors have connecting cables, respectively, with said connecting cables being of different shapes relative to one another, and said connecting terminals of said terminal unit have different shapes relative to one another, with the different shapes of said connecting cables corresponding to the different shapes of said connecting terminals such that only when the shape of one of said connecting cables and the shape of one of said connecting terminals match with each other, can said one of said connecting cables and said one of said connecting terminals be electrically connected together.

48. A biodata interfacing device comprising:

a main control unit;

measuring instruments for collecting biodata from a patient and converting the biodata into physical signals;

a terminal unit including connecting terminals corresponding to said measuring instruments, respectively, and for transmitting the biodata therefrom to said main control unit; and an operating unit and a voice output unit through which a user is to communicate with said main control unit, such that when the user selects one of said measuring instruments via said operating unit, said main control unit cause of said voice output unit to provide the user with an audio indication of one of said connecting terminals that corresponds to said one of said measuring instruments.

49. The biodata interfacing device according to claim 48, wherein said sensors have connecting cables, respectively, with said connecting cables being of different shapes relative to one another, and said connecting terminals of said terminal unit have different shapes relative to one another, with the different shapes of said connecting cables corresponding to the different shapes of said connecting terminals such that only when the shape of one of said connecting cables and the shape of one of said connecting terminals match with each other, can said one of said connecting cables and said one of said connecting terminals be electrically connected together.

50. A biodata interfacing device comprising:

a service console;

an attachment storage compartment defined in said service console for accommodating a variety of sensors used for collecting biodata;

a lid mounted on said service console for opening and closing a top opening of said attachment storage compartment;

an instrument canister to accommodate therein the variety of sensors, such that said instrument canister enables the variety of sensors to be accommodated within said attachment storage compartment in an arrangement of the variety of sensors as accommodated within said instrument canister;

identifying structure on said instrument canister for identifying a type of said instrument canister;

a reading device provided in said service console for reading said identifying structure; and a mode override device for changing a mode of operation of the biodata interfacing device according to a result of reading of said identifying structure by said reading device.

51. A biodata interfacing device comprising:

a service console;

an attachment storage compartment defined in said service console for accommodating a variety of sensors that are to be used for collecting biodata;

a lid mounted on said service console for opening and closing a top opening of said attachment storage compartment;

a display unit on said upper surface of said lid; and a camera unit detachably provided on an outer surface of said service console, wherein said instrument storage compartment is capable of accommodating therein at least one of a camera body, a camera support and a holder of said camera unit.

52. A biodata interfacing device comprising:

a service console;

an attachment storage compartment defined in said service console for accommodating a variety of sensors that are to be used for collecting biodata;

a lid mounted on said service console for opening and closing a top opening of said attachment storage compartment;

a display unit on said upper surface of said lid;

a camera unit detachably provided on an outer surface of said service console;

a microphone provided in said service console; and a support member in front of said microphone for supporting a sensor for outputting a voice signal.

53. The biodata interfacing according to claim 52, wherein said support member in front of said microphone is removable or slidable according to a shape of the sensor for outputting the voice signal.

* * * * *